United States Patent
Block et al.

(10) Patent No.: US 11,635,786 B2
(45) Date of Patent: Apr. 25, 2023

(54) ELECTRONIC OPTICAL SENSING DEVICE

(71) Applicant: Apple Inc., Cupertino, CA (US)

(72) Inventors: Ueyn L. Block, Menlo Park, CA (US); Devon K. Copeland, Sunnyvale, CA (US); Guocheng Shao, Campbell, CA (US); Vivek Venugopal, Sunnyvale, CA (US)

(73) Assignee: APPLE INC., Cupertino, CA (US)

( * ) Notice: Subject to any disclaimer, the term of this patent is extended or adjusted under 35 U.S.C. 154(b) by 87 days.

(21) Appl. No.: 17/019,172

(22) Filed: Sep. 11, 2020

(65) Prior Publication Data

US 2021/0389798 A1 Dec. 16, 2021

Related U.S. Application Data

(60) Provisional application No. 63/037,961, filed on Jun. 11, 2020.

(51) Int. Cl.
*H04B 17/27* (2015.01)
*H04B 1/3827* (2015.01)
(Continued)

(52) U.S. Cl.
CPC ............ *G06F 1/163* (2013.01); *G06F 1/1626* (2013.01); *G06F 1/1628* (2013.01);
(Continued)

(58) Field of Classification Search
CPC ...... G06F 1/163; G06F 1/1626; G06F 1/1628; H04B 17/27; H04B 1/385;
(Continued)

(56) References Cited

U.S. PATENT DOCUMENTS 2,771,734 A 11/1956 Ernest
3,040,514 A 6/1962 Hyman
(Continued)

FOREIGN PATENT DOCUMENTS

CN 1445627 A 10/2003
CN 1624427 A 6/2005
(Continued)

OTHER PUBLICATIONS

International Search Report and Written Opinion, PCT/US2013/045264, dated Mar. 25, 2014, 10 pages.
(Continued)

*Primary Examiner* — Allen L Parker
*Assistant Examiner* — David W Houston, III
(74) *Attorney, Agent, or Firm* — Dorsey & Whitney LLP

(57) ABSTRACT

An electronic device can include a housing that includes an optically transparent component. First and second light emitters can be positioned in the internal volume defined by the housing. A light detector can be positioned in the internal volume and can be optically isolated from the first and second light emitters within the internal volume. An opaque material can be disposed on the optically transparent component and can be positioned to inhibit light emitted from the second light emitter from reaching the light detector and to allow light emitted from the first light emitter to reach the light detector.

20 Claims, 20 Drawing Sheets

(51) Int. Cl.
*H01L 27/146* (2006.01)
*H01L 31/0232* (2014.01)
*H05K 5/00* (2006.01)
*G06F 1/16* (2006.01)
*H01Q 1/27* (2006.01)

(52) U.S. Cl.
CPC .. *H01L 27/14618* (2013.01); *H01L 27/14627* (2013.01); *H01L 31/0232* (2013.01); *H01Q 1/273* (2013.01); *H04B 1/385* (2013.01); *H04B 17/27* (2015.01); *H05K 5/0017* (2013.01)

(58) Field of Classification Search
CPC ......... H01L 27/14618; H01L 27/14627; H01L 31/0232; H01Q 1/273; H05K 5/0017
USPC ...................................................... 257/432
See application file for complete search history.

(56) References Cited

U.S. PATENT DOCUMENTS

| | | |
|---|---|---|
| 3,056,030 A | 9/1962 | Kelchner |
| 3,130,539 A | 4/1964 | Davis |
| 3,355,873 A | 12/1967 | Ernest |
| 3,495,398 A | 2/1970 | Widmer et al. |
| 3,621,649 A | 11/1971 | Vulcan et al. |
| 4,007,347 A | 2/1977 | Haber |
| 4,031,341 A | 6/1977 | Wuthrich et al. |
| 4,037,068 A | 7/1977 | Gaynor |
| 4,077,200 A | 3/1978 | Schneider |
| 4,133,404 A | 1/1979 | Griffin |
| 4,170,104 A | 10/1979 | Yamagata |
| 4,258,096 A | 3/1981 | Lamarche |
| 4,287,400 A | 9/1981 | Kitik et al. |
| 4,289,400 A | 9/1981 | Kubota et al. |
| 4,311,990 A | 1/1982 | Burke |
| 4,324,956 A | 4/1982 | Sakakino et al. |
| 4,345,119 A | 8/1982 | Latasiewicz |
| 4,364,674 A | 12/1982 | Tesch |
| 4,379,642 A | 4/1983 | Meyrat |
| 4,417,824 A | 11/1983 | Paterson et al. |
| 4,581,509 A | 4/1986 | Sanford et al. |
| 4,600,316 A | 7/1986 | Besson |
| 4,617,461 A | 10/1986 | Subbarao et al. |
| 4,641,026 A | 2/1987 | Garcia, Jr. |
| 4,670,737 A | 6/1987 | Rilling |
| 4,783,772 A | 11/1988 | Umemoto et al. |
| 4,884,073 A | 11/1989 | Souloumiac |
| 4,922,070 A | 5/1990 | Dorinski |
| 4,931,794 A | 6/1990 | Haag et al. |
| 4,952,799 A | 8/1990 | Loewen |
| 4,980,658 A | 12/1990 | Miner et al. |
| 5,034,602 A | 7/1991 | Garcia, Jr. et al. |
| 5,214,278 A | 5/1993 | Banda |
| 5,258,592 A | 11/1993 | Nishikawa et al. |
| 5,288,993 A | 2/1994 | Bidiville et al. |
| 5,347,123 A | 9/1994 | Jackson et al. |
| 5,383,166 A | 1/1995 | Gallay |
| 5,471,054 A | 11/1995 | Watanabe |
| 5,572,314 A | 11/1996 | Hyman, Jr. et al. |
| 5,583,560 A | 12/1996 | Florin et al. |
| 5,726,645 A | 3/1998 | Kamon et al. |
| 5,748,111 A | 5/1998 | Bates |
| 5,841,050 A | 11/1998 | Clift et al. |
| 5,847,335 A | 12/1998 | Sugahara et al. |
| 5,867,082 A | 2/1999 | Van Zeeland |
| 5,943,233 A | 8/1999 | Ebina et al. |
| 5,953,001 A | 9/1999 | Challener et al. |
| 5,963,332 A | 10/1999 | Feldman et al. |
| 6,069,567 A | 5/2000 | Zawilski |
| 6,134,189 A | 10/2000 | Carrard |
| 6,154,201 A | 11/2000 | Levin et al. |
| 6,175,679 B1 | 1/2001 | Veligdan et al. |
| 6,246,050 B1 | 6/2001 | Tullis et al. |
| 6,252,825 B1 | 6/2001 | Perotto |
| 6,304,247 B1 | 10/2001 | Black |
| 6,355,891 B1 | 3/2002 | Ikunami |
| 6,422,740 B1 | 7/2002 | Leuenberger |
| 6,477,117 B1 | 11/2002 | Narayanaswami et al. |
| 6,525,278 B2 | 2/2003 | Villain et al. |
| 6,556,222 B1 | 4/2003 | Narayanaswami |
| 6,641,438 B1 | 11/2003 | Billman |
| 6,646,635 B2 | 11/2003 | Pogatetz et al. |
| 6,661,438 B1 | 12/2003 | Shiraishi et al. |
| 6,672,758 B2 | 1/2004 | Ehrsam et al. |
| 6,794,992 B1 | 9/2004 | Rogers |
| 6,809,275 B1 | 10/2004 | Cheng et al. |
| 6,888,076 B2 | 5/2005 | Hetherington |
| 6,909,378 B1 | 6/2005 | Lambrechts et al. |
| 6,914,551 B2 | 7/2005 | Vidal |
| 6,961,099 B2 | 11/2005 | Takano et al. |
| 6,963,039 B1 | 11/2005 | Weng et al. |
| 6,964,099 B1 | 11/2005 | Zeng |
| 6,985,107 B2 | 1/2006 | Anson et al. |
| 6,987,568 B2 | 1/2006 | Dana |
| 6,998,553 B2 | 2/2006 | Hisamune et al. |
| 7,016,263 B2 | 3/2006 | Gueissaz et al. |
| 7,081,905 B1 | 7/2006 | Raghunath |
| 7,119,289 B2 | 10/2006 | Lacroix |
| 7,135,673 B2 | 11/2006 | Saint |
| 7,167,083 B2 | 1/2007 | Giles |
| 7,244,927 B2 | 7/2007 | Huynh |
| 7,265,336 B2 | 9/2007 | Hataguchi et al. |
| 7,274,303 B2 | 9/2007 | Dresti et al. |
| 7,358,481 B2 | 4/2008 | Yeoh et al. |
| 7,369,308 B2 | 5/2008 | Tsuruta et al. |
| 7,404,667 B2 | 7/2008 | Born et al. |
| 7,465,917 B2 | 12/2008 | Chin et al. |
| 7,520,664 B2 | 4/2009 | Wai |
| 7,528,824 B2 | 5/2009 | Kong |
| 7,545,367 B2 | 6/2009 | Sunda et al. |
| 7,593,755 B2 | 9/2009 | Colando et al. |
| 7,605,846 B2 | 10/2009 | Watanabe |
| 7,634,263 B2 | 12/2009 | Louch et al. |
| 7,646,667 B2 | 1/2010 | Conley et al. |
| 7,646,677 B2 | 1/2010 | Nakamura |
| 7,710,456 B2 | 5/2010 | Koshiba |
| 7,761,246 B2 | 7/2010 | Matsui |
| 7,763,819 B2 | 7/2010 | Ieda et al. |
| 7,772,507 B2 | 8/2010 | Orr et al. |
| 7,778,115 B2 | 8/2010 | Ruchonnet |
| 7,781,726 B2 | 8/2010 | Matsui et al. |
| RE41,637 E | 9/2010 | Ohara et al. |
| 7,791,597 B2 | 9/2010 | Silverstein et al. |
| 7,856,255 B2 | 12/2010 | Tsuchiya et al. |
| 7,858,583 B2 | 12/2010 | Schmidt, Jr. et al. |
| 7,865,324 B2 | 1/2011 | Lindberg et al. |
| 8,063,892 B2 | 11/2011 | Shahoian et al. |
| 8,138,488 B2 | 3/2012 | Grot |
| 8,167,126 B2 | 5/2012 | Stiehl |
| 8,169,402 B2 | 5/2012 | Shahoian et al. |
| 8,188,989 B2 | 5/2012 | Levin et al. |
| 8,195,313 B1 | 6/2012 | Fadell et al. |
| 8,220,987 B2 | 7/2012 | Kimura et al. |
| 8,248,815 B2 | 8/2012 | Yang et al. |
| 8,263,886 B2 | 9/2012 | Lin et al. |
| 8,263,889 B2 | 9/2012 | Takahashi et al. |
| 8,305,171 B2 | 11/2012 | Kimura et al. |
| 8,312,495 B2 | 11/2012 | Vanderhoff |
| 8,368,677 B2 | 2/2013 | Yamamoto |
| 8,371,745 B2 | 2/2013 | Manni |
| 8,373,661 B2 | 2/2013 | Lan et al. |
| 8,410,971 B2 | 4/2013 | Friedlander |
| 8,432,368 B2 | 4/2013 | Momeyer et al. |
| 8,439,559 B2 | 5/2013 | Luk et al. |
| 8,441,450 B2 | 5/2013 | Degner et al. |
| 8,446,713 B2 | 5/2013 | Lai |
| 8,477,118 B2 | 7/2013 | Lan et al. |
| 8,493,190 B2 | 7/2013 | Periquet et al. |
| 8,525,777 B2 | 9/2013 | Stavely et al. |
| 8,568,313 B2 | 10/2013 | Sadhu |
| 8,576,044 B2 | 11/2013 | Chapman |
| 8,593,598 B2 | 11/2013 | Chen et al. |

(56) References Cited

U.S. PATENT DOCUMENTS

| | | | |
|---|---|---|---|
| 8,614,881 B2 | 12/2013 | Yoo | |
| 8,666,682 B2 | 3/2014 | Lavigne et al. | |
| 8,704,787 B2 | 4/2014 | Yamamoto et al. | |
| 8,711,093 B2 | 4/2014 | Ong et al. | |
| 8,724,087 B2 | 5/2014 | Van De Kerkhof et al. | |
| 8,730,167 B2 | 5/2014 | Ming et al. | |
| 8,743,088 B2 | 6/2014 | Watanabe | |
| 8,783,944 B2 | 7/2014 | Doi | |
| 8,804,993 B2 | 8/2014 | Shukla et al. | |
| 8,824,245 B2 | 9/2014 | Lau et al. | |
| 8,847,741 B2 | 9/2014 | Birnbaum et al. | |
| 8,859,971 B2 | 10/2014 | Weber et al. | |
| 8,860,674 B2 | 10/2014 | Lee et al. | |
| 8,863,219 B2 | 10/2014 | Brown et al. | |
| 8,878,657 B2 | 11/2014 | Periquet et al. | |
| 8,885,856 B2 | 11/2014 | Sacha | |
| 8,895,911 B2 | 11/2014 | Takahashi | |
| 8,920,022 B2 | 12/2014 | Ishida et al. | |
| 8,922,399 B2 | 12/2014 | Bajaj et al. | |
| 8,928,452 B2 | 1/2015 | Kim et al. | |
| 8,994,827 B2 | 3/2015 | Mistry et al. | |
| 9,024,733 B2 | 5/2015 | Wouters | |
| 9,041,663 B2 | 5/2015 | Westerman | |
| 9,086,738 B2 | 7/2015 | Leung et al. | |
| 9,105,413 B2 | 8/2015 | Hiranuma et al. | |
| 9,123,483 B2 | 9/2015 | Ferri et al. | |
| 9,176,598 B2 | 11/2015 | Sweetser et al. | |
| 9,213,409 B2 | 12/2015 | Redelsheimer et al. | |
| 9,223,296 B2 | 12/2015 | Yang et al. | |
| 9,449,770 B2 | 9/2016 | Sanford et al. | |
| 9,829,350 B2 | 11/2017 | Holenarsipur et al. | |
| 10,165,694 B1 | 12/2018 | Werner et al. | |
| 10,732,571 B2 | 8/2020 | Ely et al. | |
| 11,181,863 B2 | 11/2021 | Ely et al. | |
| 2001/0053109 A1 | 12/2001 | Ehrsam et al. | |
| 2003/0160680 A1 | 8/2003 | Hisamune et al. | |
| 2003/0174590 A1 | 9/2003 | Arikawa et al. | |
| 2004/0082414 A1 | 4/2004 | Knox | |
| 2005/0075558 A1 | 4/2005 | Vecerina et al. | |
| 2005/0164623 A1 | 7/2005 | Huynh | |
| 2006/0250377 A1 | 11/2006 | Zadesky et al. | |
| 2007/0013775 A1 | 1/2007 | Shin | |
| 2007/0050054 A1 | 3/2007 | Sambandam et al. | |
| 2007/0122076 A1 | 5/2007 | Ishiyama et al. | |
| 2007/0124772 A1 | 5/2007 | Bennett et al. | |
| 2007/0211042 A1 | 9/2007 | Kim et al. | |
| 2007/0222756 A1 | 9/2007 | Wu et al. | |
| 2007/0229671 A1 | 10/2007 | Takeshita et al. | |
| 2007/0247421 A1 | 10/2007 | Orsley et al. | |
| 2008/0067050 A1 | 3/2008 | Ieda et al. | |
| 2008/0097221 A1* | 4/2008 | Florian | A61B 5/14552 600/476 |
| 2008/0130914 A1 | 6/2008 | Cho | |
| 2008/0297372 A1 | 12/2008 | Wouters | |
| 2009/0051649 A1 | 2/2009 | Rondel | |
| 2009/0073119 A1 | 3/2009 | Phan et al. | |
| 2009/0146975 A1 | 6/2009 | Chang | |
| 2009/0152452 A1 | 6/2009 | Lee et al. | |
| 2009/0217207 A1 | 8/2009 | Kagermeier et al. | |
| 2009/0285443 A1 | 11/2009 | Camp, Jr. et al. | |
| 2009/0312051 A1 | 12/2009 | Hansson et al. | |
| 2009/0322583 A1 | 12/2009 | Reams et al. | |
| 2010/0033430 A1 | 2/2010 | Kakutani et al. | |
| 2010/0053468 A1 | 3/2010 | Harvill | |
| 2010/0081375 A1 | 4/2010 | Rosenblatt et al. | |
| 2010/0149099 A1 | 6/2010 | Elias | |
| 2010/0187074 A1 | 7/2010 | Manni | |
| 2011/0007468 A1 | 1/2011 | Burton et al. | |
| 2011/0037609 A1 | 2/2011 | Kim et al. | |
| 2011/0090148 A1 | 4/2011 | Li et al. | |
| 2011/0235471 A1 | 9/2011 | Luk et al. | |
| 2012/0041925 A1 | 2/2012 | Pope et al. | |
| 2012/0067711 A1 | 3/2012 | Yang | |
| 2012/0068833 A1 | 3/2012 | Rothkopf et al. | |
| 2012/0068857 A1 | 3/2012 | Rothkopf et al. | |
| 2012/0075082 A1 | 3/2012 | Rothkopf et al. | |
| 2012/0106063 A1* | 5/2012 | Mathew | G02F 1/133528 349/110 |
| 2012/0112859 A1 | 5/2012 | Park et al. | |
| 2012/0113044 A1 | 5/2012 | Strazisar et al. | |
| 2012/0206248 A1 | 8/2012 | Biggs | |
| 2013/0001724 A1* | 1/2013 | Masuda | H01L 27/14627 257/E31.127 |
| 2013/0037396 A1 | 2/2013 | Yu | |
| 2013/0087443 A1 | 4/2013 | Kikuchi | |
| 2013/0163395 A1 | 6/2013 | Ferri et al. | |
| 2013/0215724 A1 | 8/2013 | Hiranuma et al. | |
| 2014/0071050 A1 | 3/2014 | Armstrong-muntner | |
| 2014/0071098 A1 | 3/2014 | You et al. | |
| 2014/0132516 A1 | 5/2014 | Tsai et al. | |
| 2014/0197936 A1 | 7/2014 | Biggs et al. | |
| 2014/0275850 A1* | 9/2014 | Venkatraman | A61B 5/02416 600/595 |
| 2014/0327630 A1 | 11/2014 | Burr et al. | |
| 2014/0340318 A1 | 11/2014 | Stringer | |
| 2015/0041289 A1 | 2/2015 | Ely | |
| 2015/0070794 A1* | 3/2015 | Wu | G02B 5/0816 359/838 |
| 2015/0130005 A1* | 5/2015 | Ko | H01L 27/14621 438/70 |
| 2015/0168178 A1 | 6/2015 | Hoover et al. | |
| 2015/0221460 A1 | 8/2015 | Teplitxky et al. | |
| 2015/0227217 A1 | 8/2015 | Fukumoto | |
| 2015/0341031 A1 | 11/2015 | Marquas et al. | |
| 2016/0054813 A1 | 2/2016 | Schediwy et al. | |
| 2016/0056194 A1* | 2/2016 | Rudmann | H01L 27/14685 257/432 |
| 2016/0058375 A1 | 3/2016 | Rothkopf | |
| 2016/0061636 A1 | 3/2016 | Gowreesunker et al. | |
| 2016/0072177 A1* | 3/2016 | Sharma | H04B 1/3827 343/702 |
| 2016/0098016 A1 | 4/2016 | Ely et al. | |
| 2016/0240721 A1* | 8/2016 | Chu | G01J 1/44 |
| 2016/0258784 A1 | 9/2016 | Boonsom et al. | |
| 2016/0306437 A1 | 10/2016 | Zhang et al. | |
| 2016/0313703 A1 | 10/2016 | Ely et al. | |
| 2016/0327911 A1 | 11/2016 | Eim et al. | |
| 2016/0378069 A1 | 12/2016 | Rothkopf | |
| 2016/0378070 A1 | 12/2016 | Rothkopf | |
| 2016/0378072 A1 | 12/2016 | Ely et al. | |
| 2016/0378081 A1 | 12/2016 | Della Corte et al. | |
| 2017/0003655 A1 | 1/2017 | Ely | |
| 2017/0010751 A1 | 1/2017 | Shedletsky et al. | |
| 2017/0011873 A1 | 1/2017 | Ely et al. | |
| 2017/0045958 A1 | 2/2017 | Battlogg | |
| 2017/0069443 A1 | 3/2017 | Wang et al. | |
| 2017/0069444 A1 | 3/2017 | Wang et al. | |
| 2017/0069447 A1 | 3/2017 | Wang et al. | |
| 2019/0079452 A1 | 3/2019 | Hiemstra et al. | |
| 2019/0198547 A1* | 6/2019 | Yoshigiwa | H01L 27/14623 |
| 2019/0227597 A1* | 7/2019 | Kim | H01L 27/14627 257/E31.127 |

FOREIGN PATENT DOCUMENTS

| | | |
|---|---|---|
| CN | 103191557 A | 7/2013 |
| CN | 103645804 A | 3/2014 |
| CN | 103852090 A | 6/2014 |
| CN | 103956006 A | 7/2014 |
| CN | 203732900 U | 7/2014 |
| CN | 103995456 A | 8/2014 |
| CN | 203941395 U | 11/2014 |
| CN | 105096979 A | 11/2015 |
| CN | 105547146 A | 5/2016 |
| DE | 102008023651 A1 | 11/2009 |
| EP | 0556155 A1 | 8/1993 |
| EP | 1345095 A2 | 9/2003 |
| EP | 1669724 A2 | 6/2006 |
| EP | 2375295 A2 | 10/2011 |
| EP | 2720129 A1 | 4/2014 |
| FR | 2030093 A1 | 10/1970 |
| FR | 2801402 A1 | 5/2001 |
| GB | 2433211 A | 6/2007 |

(56) References Cited

FOREIGN PATENT DOCUMENTS

| | | |
|---|---|---|
| JP | S5734457 A | 2/1982 |
| JP | H05203465 A | 8/1993 |
| JP | 2001202178 A | 7/2001 |
| JP | 2003151410 A | 5/2003 |
| JP | 2003331693 A | 11/2003 |
| JP | 2004184396 A | 7/2004 |
| JP | 2007311153 A | 11/2007 |
| JP | 2008053980 A | 3/2008 |
| JP | 2008122377 A | 5/2008 |
| JP | 2008235226 A | 10/2008 |
| JP | 2010186572 A | 8/2010 |
| JP | 2011165468 A | 8/2011 |
| KR | 20080045397 A | 5/2008 |
| NL | 1040225 C2 | 11/2014 |
| WO | 0122038 A1 | 3/2001 |
| WO | 0169567 A2 | 9/2001 |
| WO | 2010058376 A2 | 5/2010 |
| WO | 2012083380 A1 | 6/2012 |
| WO | 2014018118 A1 | 1/2014 |
| WO | 2015147756 A1 | 10/2015 |

OTHER PUBLICATIONS

International Search Report and Written Opinion for PCT/US2014/050358, dated Nov. 10, 2014, 10 pages.
International Search Report and Written Opinion, PCT/US2014/040728, dated Oct. 15, 2014, 14 pages.
Author Unknown, ""mHealth"", http://mhealth.vesag.com/?m=201012, Dec. 23, 2010, 7 pages.
Author Unknown, "DeskThorityNet, Optical Switch Keyboards", http://deskthority.net/keyboards-f2/optical-switch-keyboards-t1474.html, Jul. 11, 2015, 22 pages.
Author Unknown, "How Vesag Helps Kids Women and Visitors", http://www.sooperarticles.com/health-fitness-articles/children-health-articles/how-vesag-helps-kids-women-visitors-218542.html, 2 pages, at least as early as May 20, 2015.
Author Unknown, "Re iPhone Universal Remote Control—Infrared Remote Control Accessory for iPhone and iPod Touch", http://www.amazon.com/iPhone-Universal-Remote-Control-Accessory/dp/tech-data/B0038Z4, at least as early as Jul. 15, 2010, 2 pages.
Author Unknown, "RedEye mini Plug-in Universal Remote for iPhone, iPodtouch and iPad", Amazon.com, date unknown, 4 pages.
Author Unknown, "Vesag Wrist Watch for Dementia Care from VYZIN", http://vyasa-kaaranam-ketkadey.blogspot.com/2011/03/vesag-wrist-watch-for-dementia-care.html, Mar. 31, 2011, 2 pages.
Author Unknown, "Vyzin Electronics Private Limited launches "Vesag Watch."", http://www.virtualpressoffice.com/showJointPage.do?page=jp&showld=1544, Jan. 6, 2011, 5 pages.
Author Unknown, "Vyzin Unveiled Personal Emergency Response System (PERS) with Remote Health Monitoring That Can Be Used for Entire Family", http://www.24-7pressrelease.com/press-release/vyzin-unveiled-personal-emergency-response-system-pers-with-remote-health-monitoring-that-can-be-used-for-entire-family-219317.php, Jun. 17, 2011, 2 pages.
Epstein, et al., "Economical, High-Performance Optical Encoders", Hewlett-Packard Journal, Oct. 1988, pp. 99-106.
Greyb, "Google Watch: Convert your arm into a keyboard", http://www.whatafuture.eom/2014/02/28/google-smartwatch/#sthash.Yk35cDXK.dpbs, Feb. 28, 2014, 3 pages.
IBM, "Additional Functionality Added to Cell Phone via "Learning" Function Button", www.ip.com, Feb. 21, 2007, 2 pages.
Kim, Joseph, "2010 mHealth Summit Emerges as Major One-Stop U.S. Venue for Mobile Health", http://www.medicineandtechnology.com/2010/08/2010-mhealth-summit-emerges-as-major.html, Aug. 26, 2010, 3 pages.
Krishnan, et al., "A Miniature Surface Mount Reflective Optical Shaft Encoder", Hewlett-Packard Journal, Article 8, Dec. 1996, pp. 1-6.
Rick, "How VESAG Helps Health Conscious Citizens", http://sensetekgroup.com/2010/11/29/wireless-health-monitoring-system/, Nov. 29, 2010, 2 pages.
Sadhu, Rajendra, "How VESAG Helps People Who Want to 'Be There'?", http://ezinearticles.com/?How-Vesag-Helps-People-Who-Want-to-Be-There?&id-5423873, Nov. 22, 2010, 1 page.
Sadhu, Rajendra, "Mobile Innovation Helps Dementia and Alzheimer's Patients", http://www.itnewsafrica.com/2010/11/mobile-innovation-helps-dementia-andalzheimer%E2%80%99s-patients/, Nov. 22, 2010, 3 pages.
Tran, et al., "Universal Programmable Remote Control/Telephone", www.ip.com, May 1, 1992, 2 pages.

\* cited by examiner

ELECTRONIC OPTICAL SENSING DEVICE

CROSS-REFERENCE TO RELATED APPLICATION(S)

This claims priority to U.S. Provisional Patent Application No. 63/037,961, filed 11 Jun. 2020, and entitled "ELECTRONIC DEVICE," the entire disclosure of which is hereby incorporated by reference.

FIELD

The described embodiments relate generally to electronic devices. More particularly, the present embodiments relate to wearable electronic devices.

BACKGROUND

Electronic devices are increasingly being designed with device portability in mind, for example, to allow users to use these devices in a wide variety of situations and environments. In the context of wearable devices, these devices can be designed to include many different functionalities and to be operated in many different locations and environments. The components of an electronic device, for example, the processors, memory, antennas, display, and other components can partially determine a level of performance of the electronic device. Further, the arrangement of these components with respect to one another in the device can also determine the level of performance of the electronic device.

Continued advances in electronic devices and their components have enabled considerable increases in performance. Existing components and structures for electronic devices can, however, limit the levels of performance of such devices. For example, while some components can achieve high levels of performance in some situations, the inclusion of multiple components in devices sized to enhance portability can limit the performance of the components, and thus, the performance of the device. Consequently, further tailoring an arrangement of components for electronic devices to provide additional or enhanced functionality, without introducing or increasing undesirable device properties, can be desirable.

SUMMARY

According to some examples of the present disclosure, an electronic device can include a housing at least partially defining an internal volume, the housing including an electromagnetically transparent portion at least partially defining an exterior surface of the electronic device. The electronic device can also include an antenna disposed in the internal volume and positioned to emit a signal at a power level through the electromagnetically transparent portion, and a sensing circuit disposed in the internal volume and positioned to receive the signal. The sensing circuit can be configured to measure a transmitted power of the signal. A processor can also be disposed in the internal volume, the processor being configured to compare the transmitted power with the power level.

According to some examples of the present disclosure, an electronic device can include a housing at least partially defining an internal volume, the housing including an optically transparent component at least partially defining an exterior surface of the electronic device, a first light emitter positioned in the internal volume, a second light emitter positioned in the internal volume, a light detector positioned in the internal volume, the light detector optically isolated from the first light emitter and the second light emitter within the internal volume, and an opaque material disposed on the optically transparent component, the opaque material positioned to inhibit light emitted from the second light emitter from reaching the light detector along a path from the second emitter, through a medium adjacent to a portion of exterior surface defined by the optically transparent component, and onto the light detector through the optically transparent component, and allow light emitted from the first light emitter to reach the light detector along a path from the first emitter, through the medium, and onto the light detector through the optically transparent component.

In some examples, the optically transparent component includes glass. The opaque material can be opaque to generally visible light, and/or specifically to green light. The opaque material can be transparent to infrared light. The opaque material can have a major dimension of 10 mm or less. The opaque material can have a thickness of 10 microns or less. The electronic device can further include a lens positioned over the opaque material. The optically transparent component can include sapphire. The optically transparent component can include a silicon dioxide layer, and the opaque material can be disposed on the silicon dioxide layer.

According to some examples, an electronic device can include a housing defining an internal volume, the housing including an optically transparent portion, a light emitter disposed in the internal volume, a first light detector disposed in the internal volume, a second light detector disposed in the internal volume, and a light blocking component disposed on an internal surface of the optically transparent portion, the light blocking component sized and positioned to prevent light emitted by the light emitter from passing out of the electronic device through the optically transparent component in a direction oriented more towards the second light detector than the first light detector and allow light emitted by the light emitter to pass out of the electronic device through the optically transparent component in a direction oriented more towards the first light detector than the second light detector.

In some examples, the light blocking component has a substantially circular shape. The light blocking component can have a diameter of 10 mm or less. The light blocking component can include a layer of ink. The layer can have a thickness of about 10 microns or less. The light emitter can include an LED. The light blocking component includes a first light blocking component and the electronic device further includes a second light blocking component positioned in the internal volume between the light emitter and the first light detector.

According to some examples, a housing for an electronic device can include a cover defining an aperture an optically transparent component positioned in the aperture and secured to the cover, the optically transparent component at least partially defining an internal surface of the housing and an external surface of the housing, a lens overlying a portion of the optically transparent component defining the internal surface, and an opaque material disposed on the portion of the optically transparent component defining the internal surface, the opaque material positioned between the optically transparent component and the lens. The opaque material can be opaque to visible light and at least partially transparent to infrared light. The lens can include a Fresnel lens. The optically transparent component can include glass.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The architecture and components of the electronic devices described herein can allow for configurations and designs that can maximize the number of functions and performance of a portable or wearable electronic device, while also allowing for the use of relatively low cost or abundant materials, and the reduction of manufacturing and assembly complexity and costs. While the use of high performance materials or highly complex components can enable high levels of device performance and functionality, these materials and components can also increase the cost of a device, thereby reducing the number of users who may be able to reasonably afford the device. Accordingly, it can be desirable to provide component designs that can incorporate relatively lower cost materials and that have relatively lower manufacturing complexity, but that still enable levels of performance and functionality that are on par with, or sufficiently close to levels achieved by devices including high performance materials and components.

These and other embodiments are discussed below with reference to FIGS. 1A-7B. However, those skilled in the art will readily appreciate that the detailed description given herein with respect to these Figures is for explanatory purposes only and should not be construed as limiting.

Figure 1A:
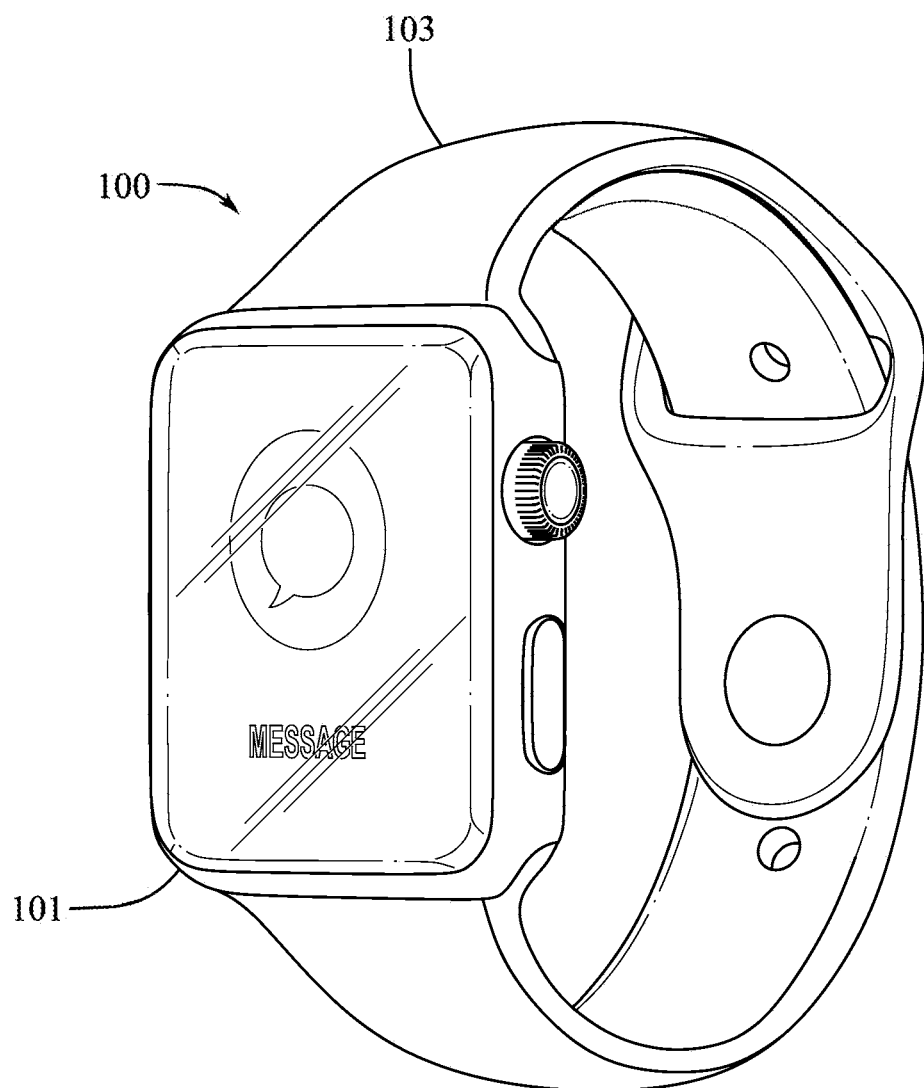
FIG. 1A shows a perspective view of an electronic device.

FIG. 1A shows an example of an electronic device 100. The electronic device shown in FIG. 1A is a watch, such as a smartwatch. The smartwatch of FIG. 1A is merely one representative example of a device that can be used in conjunction with the systems and methods disclosed herein. Electronic device 100 can correspond to any form of wearable electronic device, a portable media player, a media storage device, a portable digital assistant ("PDA"), a tablet computer, a computer, a mobile communication device, a GPS unit, a remote control device, or other electronic device. The electronic device 100 can be referred to as an electronic device, or a consumer device. In some examples, the electronic device 100 can include a body 101 that can carry operational components, for example, in an internal volume at least partially defined by a housing of the body. The electronic device 100 can also include a strap 103, or another retaining component that can secured the device 100 to a body of a user, as desired. Further details of the electronic device are provided below with reference to FIG. 1B.

Figure 1B:
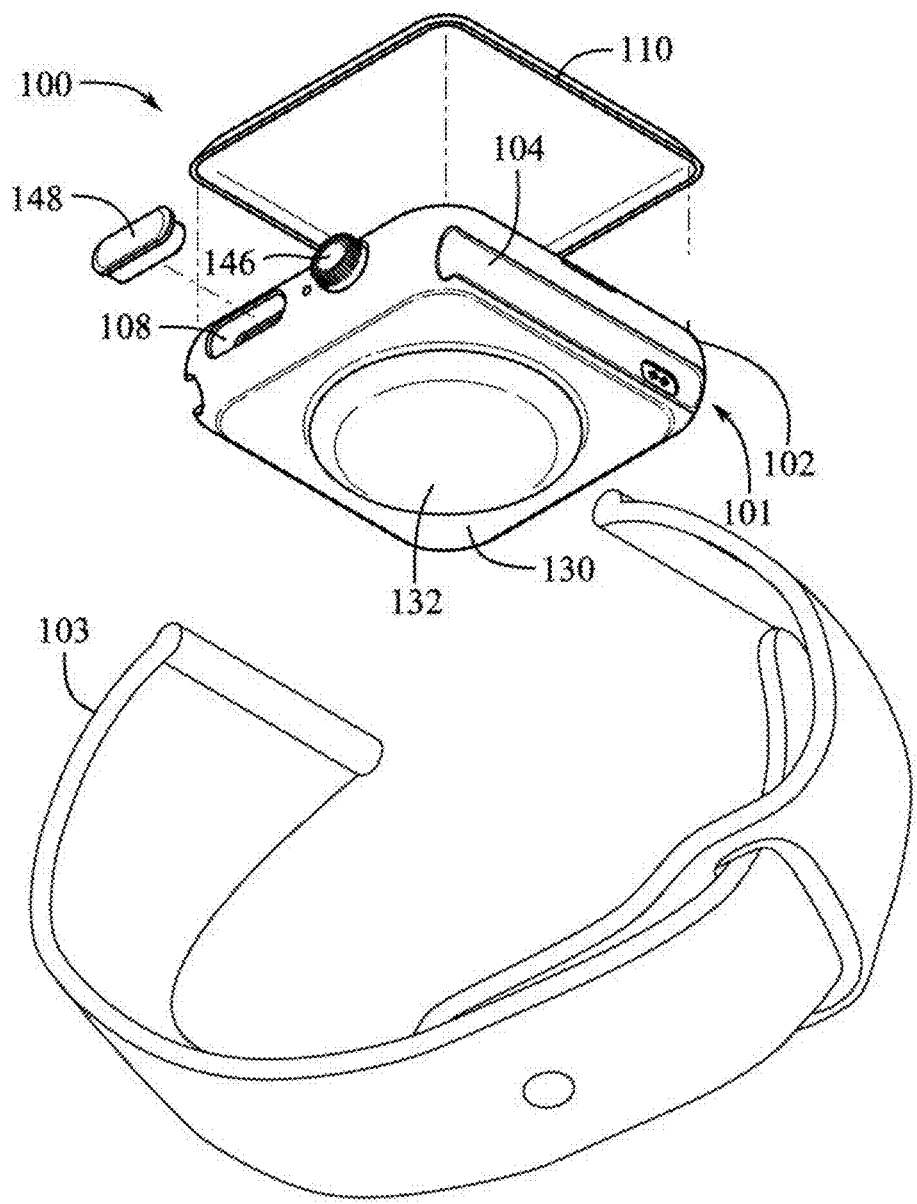
FIG. 1B shows a bottom exploded view of the electronic device of FIG. 1A.

Referring now to FIG. 1B, the electronic device 100 can include a body 101 having a housing 102 and a cover 110 attached to the housing 102. The housing 102 can substantially define at least a portion of an exterior surface of the device 100. The cover 110 can include a ceramic material such as sapphire, glass, plastic, or any other substantially transparent material, component, or assembly. The cover 110 can cover or otherwise overlay a display, a camera, a touch sensitive surface such as a touchscreen, or other component of the device 100. The cover 110 can define a front exterior surface of the device 100. Together, the housing 102 and cover 110 can substantially define the exterior surface of the device 100.

In some examples, the housing 102 can include a component 130 that defines at least an exterior surface of the device 100. The component 130 can be referred to as a back case or a back cover, and in some examples, can be attached to one or more other components, such as the housing 102. The component 130 can be attached to the housing 102 by any method known in the art or developed in the future, such as adhesive bonding, brazing, welding, overmolding, interference fitting, or other securing methods.

The back cover 130 can define one or more apertures or through holes. A transparent material 132 can be disposed in the one or more apertures. In some examples, the transparent material 132 can be visually transparent and can include any transparent including a ceramic material such as sapphire. The transparent material 132 can provide visual and electromagnetic access to an exterior environment for one or more components of the device 100, as described herein.

The housing 102 can include one or more features to receive or couple to other components of the device 100. For example, housing 102 can include features, such as an indentation 104 to receive strap 103, and an aperture 108 to receive a button 148. The housing can also define one or more apertures to receive additional input components, such as a dial or a crown 146.

The device 100 is merely one example of an electronic device 100. Additional electronic devices and designs thereof, are expressly contemplated. Further details of example electronic devices and components are provided below with reference to FIG. 2.

Figure 2:
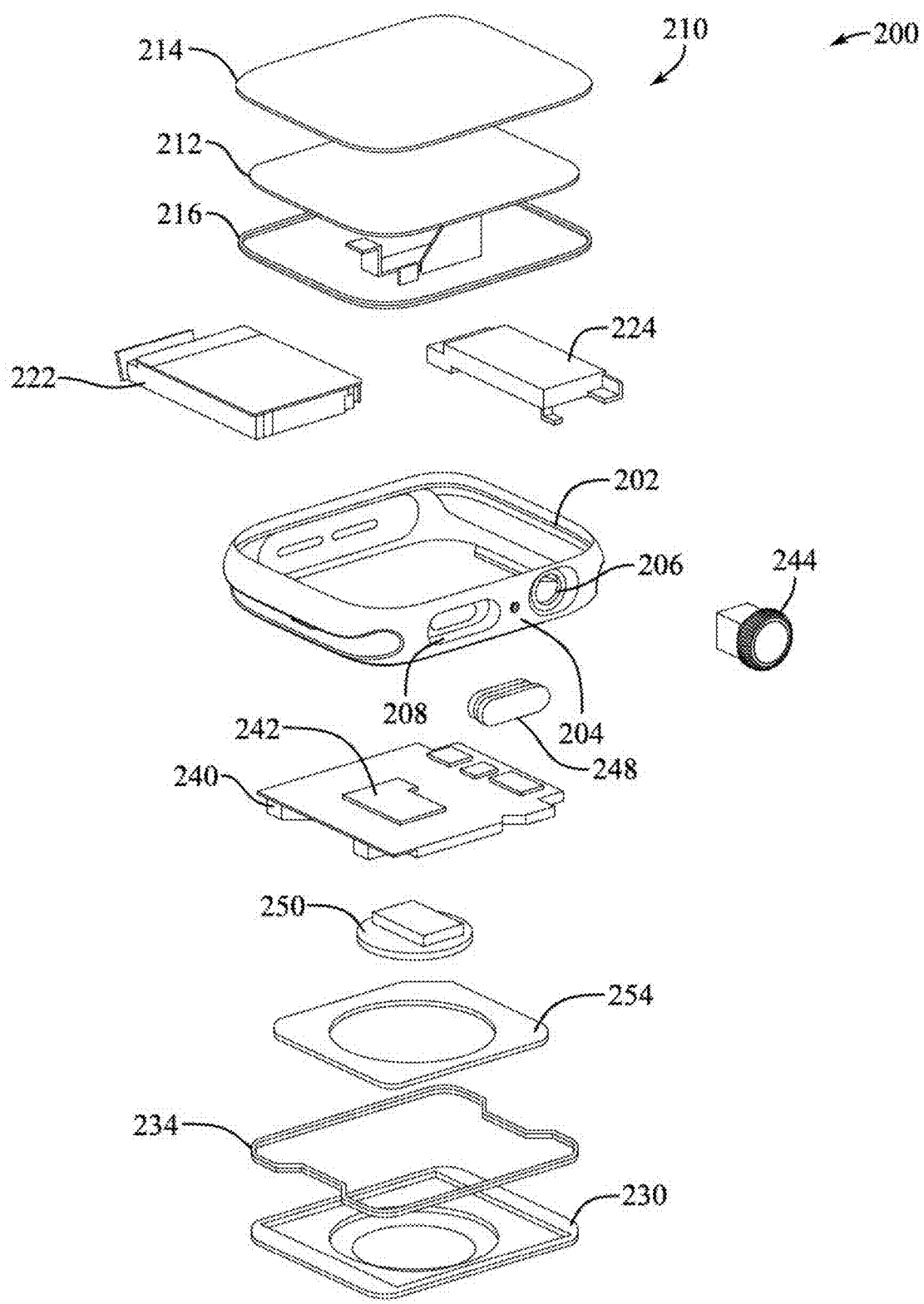
FIG. 2 shows an exploded view of an electronic device.

FIG. 2 illustrates an exploded view of a smartwatch 200 that can be substantially similar to, and can include some or all of the features of the devices described herein, such as electronic device 100. The device 200 can include a housing 202, a display assembly 210, and a back cover 230. Together, the housing 202, the display assembly 210, and the back cover 230 can define an exterior surface and an internal volume of the device 200.

The housing 202 can be a substantially continuous or unitary component, and can define one or more openings 204, 206, 208 to receive components of the electronic device 200 and/or to provide access to an internal portion of the electronic device 200. In some examples, the device 200 can include input components such as one or more buttons 248 and/or a crown 244 that can be disposed in the openings 206, 208. A microphone can be disposed in the internal volume such that it is in communication with the external or ambient environment through the opening 204.

The display assembly 210 can be received by and can be attached to the housing 202. The display assembly can include a cover 214 including a transparent material, such as plastic, glass, and/or ceramic. The display assembly 210 can also include a display stack 212 that can include multiple layers and components, each of which can perform one or more desired functions. For example, the display stack 212 can include a display layer 212 that can include a touch detection layer or component, a force sensitive layer or component, and one or more display layers or components that can include one or more pixels and/or light emitting portions to display visual content and/or information to a user. In some examples, the display layer or component 212 can include a liquid crystal display (LCD), a light emitting diode (LED) display, an organic light emitting diode (OLED) display, and/or any other form of display. The display layer 212 can also include one or more electrical connectors to provide signals and/or power to the display layer 212 from other components of the device 200.

In some examples, the device 200 can include a gasket or a seal 216 that can be disposed between the display assembly 210 and the housing 202 to substantially define a barrier to the ingress of liquids or moisture into the internal volume from the external environment at the location of the seal 216. As described herein, the seal 216 can include polymer, metal, and/or ceramic materials. The device 200 can also include a seal 234 that can be disposed between the housing 202 and the back cover 230 to substantially define a barrier to the ingress of liquids or moisture into the internal volume from the external environment at the location of the seal 234. As described herein, the seal 234 can include polymer, metal, and/or ceramic materials. The seal 234 can be substantially similar to and can include some or all of the features of the seal 216.

The device 200 can also include internal components, such as a haptic engine 224, a battery 222, and a logic board 240, also referred to as a main logic board 240, that can include a system in package (SiP) 242 disposed thereon, including one or more integrated circuits, such as processors, sensors, and memory. The SiP can also include a package.

In some examples, internal components can be disposed below the main logic board 240 and can be disposed at least partially in a portion of the internal volume defined by the back cover 230. For example, the device 200 can include an electromagnetic shielding component, otherwise referred to as an e-shield 252, that can shield other components in the device 200 from electromagnetic radiation from the ambient environment and/or as emitted by other components in the device 200. The device 200 can also include a second logic board 250 that can be in communication with one or more sensors or emitters of the device 200, for example, to receive information or signals from an external environment. In some examples, the second logic board 250 can also include a SiP. In some examples, the device 200 can include one or more wireless antennas, such as antenna 254, that can be in electrical communication with one or more other components of the device 200. In some examples, the antenna 254 can receive and/or transmit wireless signals at one or more frequencies and can be, for example, one or more of a cellular antenna such as an LTE antenna, a Wi-Fi antenna, a Bluetooth antenna, a GPS antenna, a multifrequency antenna, and the like. The antenna 254 can be communicatively coupled to one or more additional components of the electronic device 200

The internal components can be disposed within the internal volume defined at least partially by the housing 202, and can be affixed to the housing 202 via internal surfaces, attachment features, threaded connectors, studs, posts, or other features, that are formed into, defined by, or otherwise part of the housing 202 and/or the cover 214 and/or back cover 330.

Any number or variety of components in any of the configurations described herein can be included in an electronic device, as described herein. The components can include any combination of the features described herein and can be arranged in any of the various configurations described herein. The structure and arrangement of components of a device, as well as the concepts regarding the use and operation of the components can apply not only to the specific examples discussed herein, but to any number of embodiments in any combination. Various examples of electronic devices and electronic device components including having various features in various arrangements are described below, with reference to FIGS. 3-4D.

Figure 3:
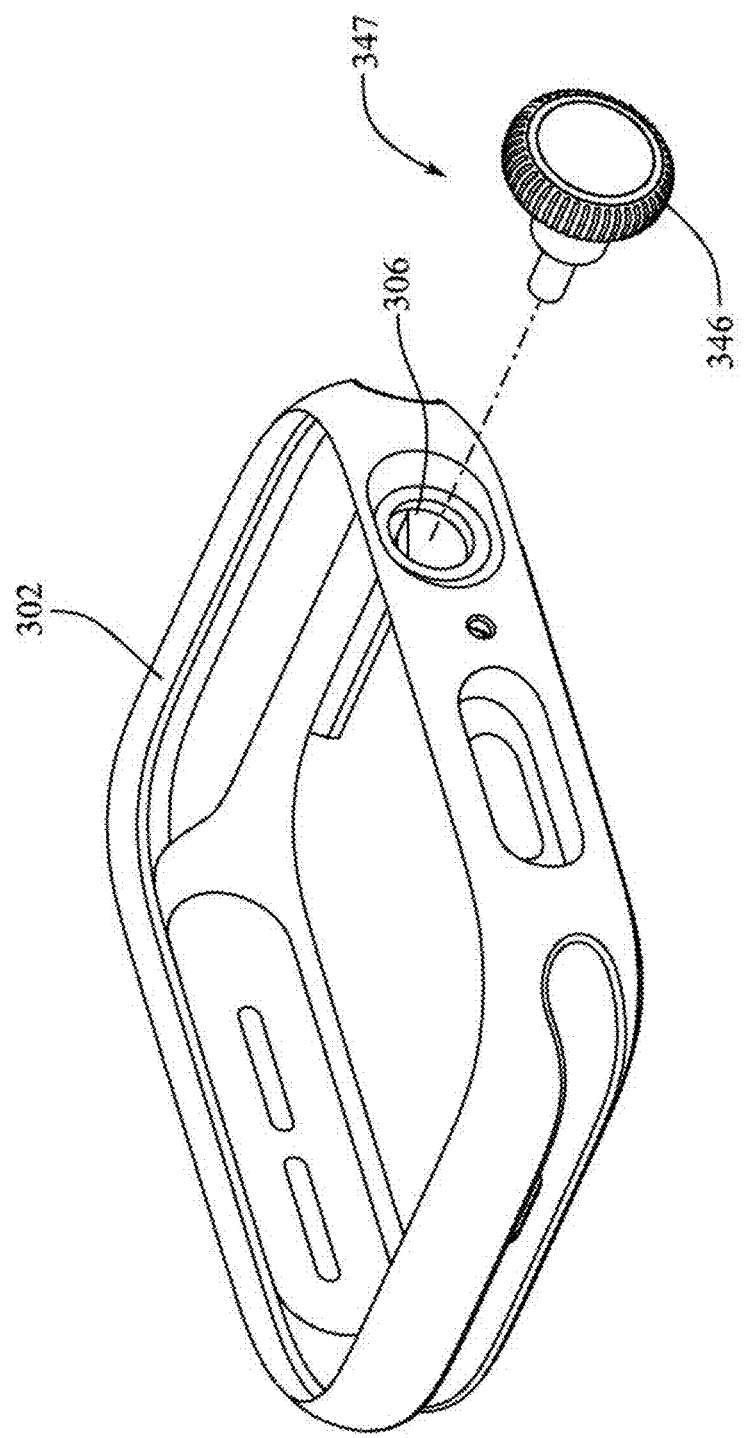
FIG. 3 shows an exploded view of a portion of an electronic device.

FIG. 3 shows an exploded view of several components of an electronic device that can be substantially similar to and can include some or all of the features of the electronic devices described herein. As described with respect to the electronic device 200 of FIG. 2, an electronic device can include a housing 302 that can at least partially define an internal volume and an input component, such as a crown or a dial 346 that can be positioned at, and at least partially extend through, an aperture 306 defined by the housing 302. The crown module 346 can be connected to one or more other components of the device (not shown).

Figure 4A:
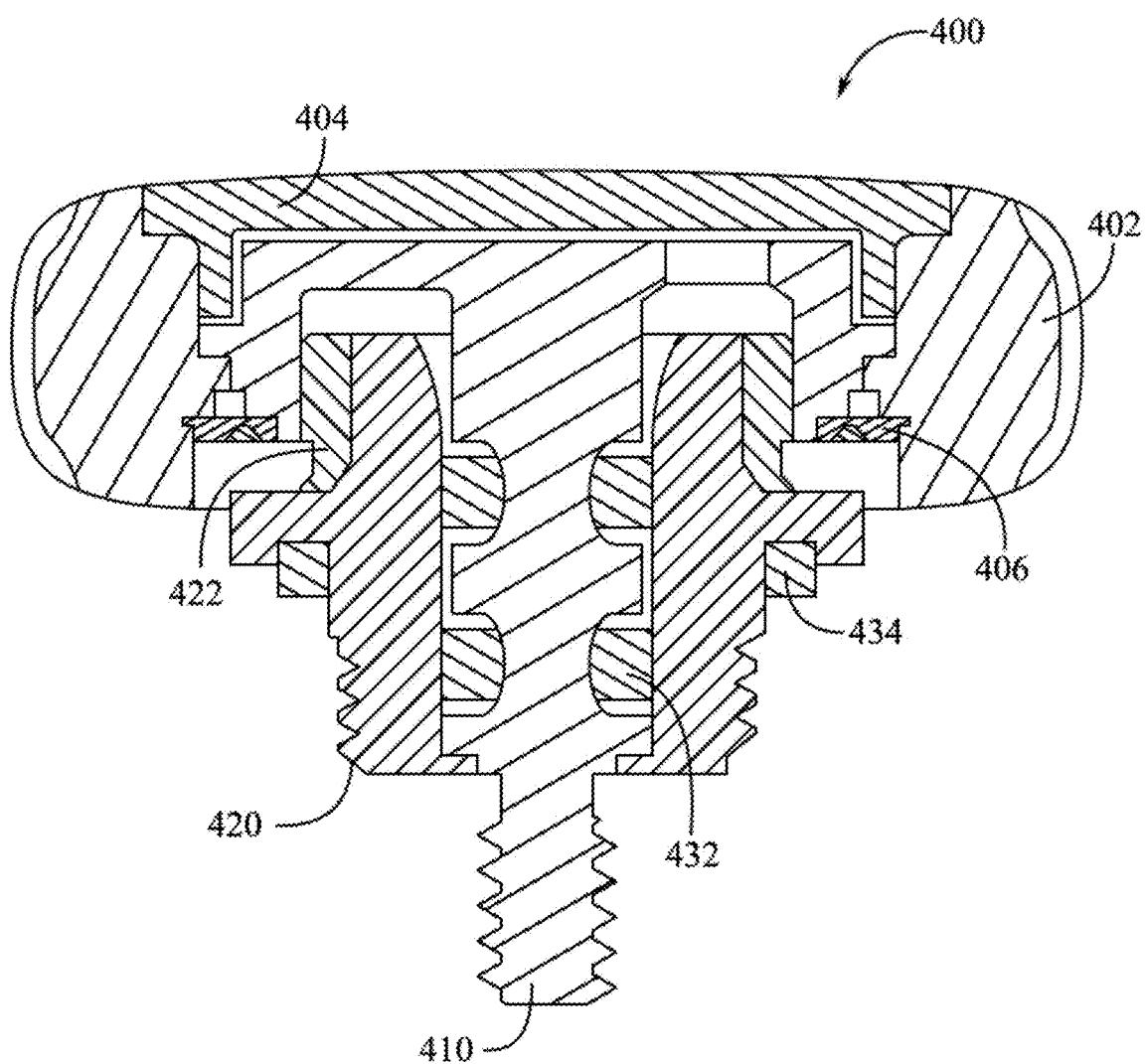
FIG. 4A shows a cross-sectional side view of a component of an electronic device.

FIG. 4A shows a cross-sectional view of an input component 400 of an electronic device. The input component 400 can be a crown or a dial of a crown module, and can be substantially similar to the dials 246, 346 described herein. In some examples, the crown 400 can be a component of a crown module that can be substantially similar to and can include some or all of the features of the crown modules described in U.S. Pat. Nos. 9,627,163 and 9,753,436, the entireties of which are incorporated by reference herein.

The input component 400 can include an outer portion or dial 402 that is connected to a shaft 410, for example, with a lock ring 406. The dial 402 can define an exterior surface of both the crown module and the electronic device including the crown module. Further, the dial 402 can be sized and shaped to be manipulated by a user, for example, to be rotated by a user about an axis defined by the shaft 410. In some examples, the dial 402 can include a cap or a ring 404 that can include a different material than the dial 402, and that can provide a desired aesthetic appearance to the exterior of the dial 402. For example, the cap 404 can be brightly colored so as to be readily identifiable by a user.

In some examples, the shaft 410 can be affixed to the lock ring 406 by any desired technique, such as one or more of an adhesive, brazing, or welding. In some examples, the shaft 410 can also include a threaded portion that can be received by other components of the crown module (not shown) and that can transmit rotational forces exerted on the dial 402 to the module. All or a portion of the shaft 410 can extend through a collar 420 that can define an aperture or an orifice through which the shaft 410 can pass. The collar 420 can house the shaft 410 and can retain the shaft 410 in a desired position. In some examples, the shaft 410 can include a protruding portion, for example, that protrudes substantially perpendicularly from a central axis of the shaft 410. In examples, the protruding portion and a central portion of the shaft can define a channel. One or more gaskets or o-rings 432 can be disposed between the shaft 410 and the collar 420 to provide or define a seal therebetween, for example, to prevent the ingress of liquid or contaminants into the internal volume of the device and/or the crown module. An additional gasket or o-ring 434 can be disposed on another surface of the collar 420 to provide or define a seal between the collar 420 and one or more other components of the crown module. In some examples, a bushing 422 can be mounted on an outer surface of the collar 420 between the collar 420 and the shaft 410, such as the protruding portion that defines the channel.

Figure 4B:
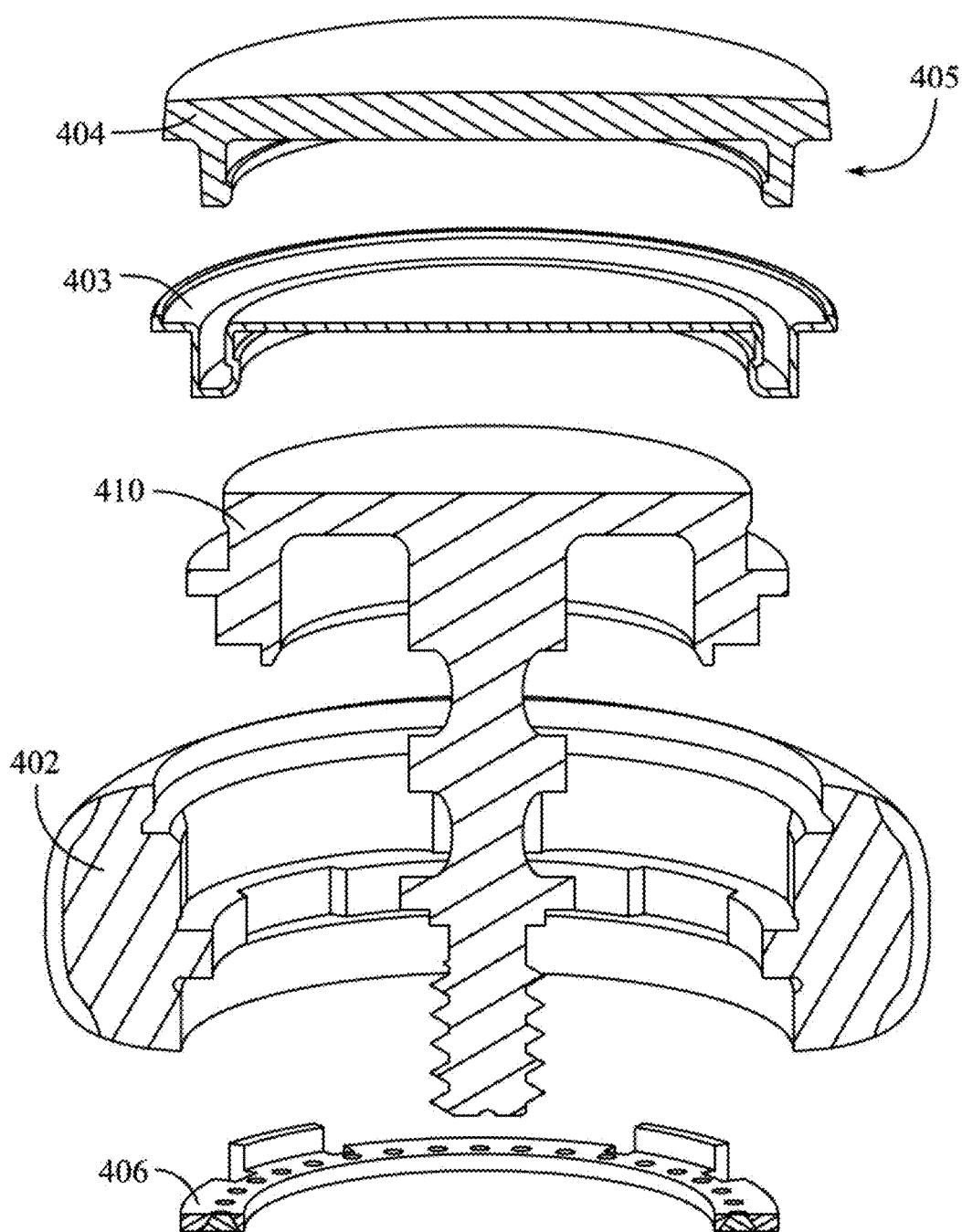
FIG. 4B shows an exploded cross-sectional view of the component of FIG. 4A.

FIG. 4B shows an exploded cross-sectional view of the dial 402 and the shaft 410. As described above, a lock ring 406 can join or affix the dial 402 to the shaft 410. In some examples, the lock ring 406 can include a metal or metallic material, such as sheet metal, including stamped sheet metal. The shaft can also include a metallic material, and in some examples, the lock ring 406 can be welded or brazed to the shaft 410, for example, to a planar surface thereof. In some examples, the lock ring 406 can have a substantially circular or ring shape, and can further include one or more protrusions that extend from the ring, such as in a direction that is substantially perpendicular to a plane of the ring. These protrusions can be sized and shaped to correspond to locking features that are defined by the dial 402 so that the protrusions can be receive and/or retained by the locking features of the dial 402. In some examples, the lock ring 406 and/or protrusions can be affixed to the dial 402 by any technique as desired such as an adhesive. In some examples, however, the lock ring 406 and/or protrusions may only be mechanically received and retained by the dial 402, for example, to prevent movement of the dial 402 relative to the shaft 410.

In some examples, the dial 402 can define a recess, a cavity, a trench, or a channel that can receive and/or retain the cap 404, for example, an engagement portion 405 thereof. In some examples, the cap 404 can have a toroidal or ring shape, however in some other examples, the cap can have a substantially circular shape, as shown. In some examples, the engagement portion 405 can extend substantially perpendicularly from a plane of the circle or ring, as shown. The cap 404 can include any desired material, such as a polymer, a metal, or a ceramic material. In some examples, the cap 404 can include a polymer material and can have any desired color, such as a bright or visually distinctive color. Thus, in some examples, the cap 404 can provide a desired cosmetic or aesthetic appearance to the dial 402 without the need for a multi-part or multi-section dial 402 architecture that can result in an undesirable increase in dial size or an undesirable increase in the distance the dial protrudes from the housing and/or crown module. The cap 404 can be retained at a desired location on the dial 402 by any desired technique. In some examples, a layer of adhesive or glue 403 can be provided in the trench defined by the dial 402 to retain the cap 404. In some other examples, a mechanical interlock between the engagement portion of the cap and a corresponding engagement feature defined by the dial 402 can additionally or alternatively retain the cap 404 in a desired position on the dial 402.

Figure 4C:
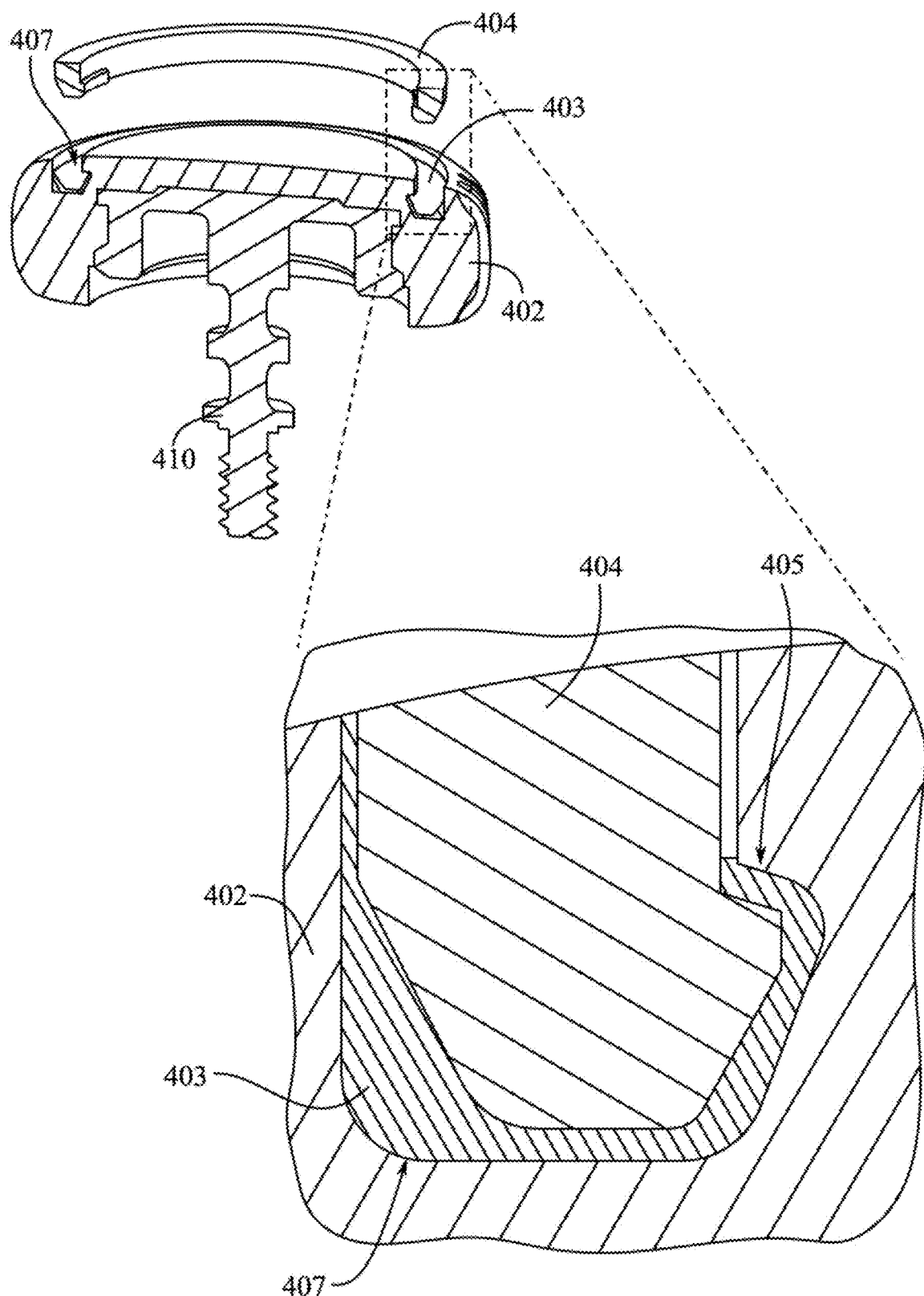
FIG. 4C shows a close-up cross-sectional view of a portion of the component of FIG. 4A.

FIG. 4C illustrates a close-up view of the engagement portion 405 of the cap 404 mating with an engagement feature 407 defined by the dial 402. As described above, the engagement feature 407 can take the form of a trench or channel. In some examples, and as shown in FIG. 4C, the channel can have an undercut geometry or can include an undercut region that can receive and retain a corresponding feature of the engagement portion 405. Thus, in some examples, the engagement portion 405 can interlock with an undercut feature in a channel defined by the dial 402. In some examples, such as where the cap 404 includes a polymer or plastic material, the cap 404 can flex and/or bend during insertion of the engagement portion 405 into the channel to allow some or all of the engagement portion 405 to snap into and/or interlock with the undercut region of the channel 407. In some examples, the undercut region can have a width of about 10 microns to about 100 microns, or about 25 microns to about 75 microns, such as about 50 microns.

In some examples, an adhesive or glue material 403 can be disposed in the channel 407 and can additionally or alternatively serve to affix the cap 404 to the dial 402. In some examples, in addition to affixing the cap 404 to the dial 402, the adhesive 403 can fill any empty volume in the channel 407 and ensure that the cap 404 is disposed at a desired depth in the channel 407, and thus relative the exterior surface of the dial 402. In some examples, the exterior surface of the cap 404 is substantially flush, level, parallel with, and/or in-plane with the exterior surface of the dial 402.

Figure 4D:
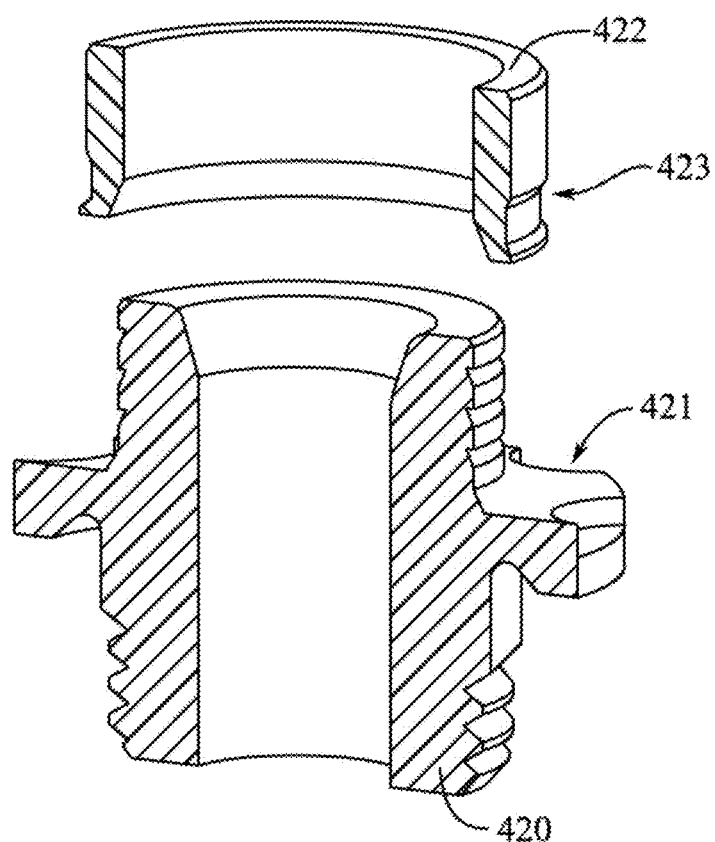
FIG. 4D shows an exploded cross-sectional view of a portion of the component of FIG. 4A.

FIG. 4D shows an exploded cross-sectional view of the collar 420 and the bushing 422, for example, as described with respect to FIG. 4A. In use, the bushing 422 can substantially surround a portion of the collar 420, such as the portion above the rim 421 that protrudes from the collar 420. In some examples, the bushing 422 can be press-fit over the collar 420 at the desired location. The collar 420 can define one or more ridges or retention features, as shown, that can retain the bushing 422 in a desired position on the collar. In some examples, the bushing 422 can be retained on the collar 420 at least partially due to an interference fit between the components. In some examples, an inner dimension of the bushing 422 can have an interference fit with an outer dimension of the collar of between about 10 microns and about 100 microns, about 25 microns and about 75 microns, or between about 30 microns and about 60 microns. In some examples, this architecture can allow for a significantly reduced height of the bushing 422 and collar 420 components, resulting in a reduce protrusion distance of the dial 402.

In some examples, the collar 420 can include a metal or metal alloy, such as steel or aluminum. In some examples, the bushing 422 can include a polymer and/or ceramic material, such as a plastic or resin. In some examples, the bushing 422 can include an acetal resin, such as DELRIN brand resin. In some examples, an inner surface of the bushing 422 can have a chamfer to allow for the press-fit process. In some examples, a height of the bushing can be about 1 mm or less, about 0.75 mm or less, or even about 0.6 mm or less. In some examples, an outer surface of the bushing 422 can define a groove or a channel 423. The groove 423 can be positioned at or near a lower edge of the bushing 422, as shown. In some examples, the components of the crown module that abut the bushing 422, such as the shaft 410, can cause wear on the bushing material over time. If no groove 423 was present, this wear could result in the formation of channel that can then have a lip. This lip could produce an undesirable sensation during depression of the dial 402 into the device, as the shaft would pass back and forth over the lip. By preemptively removing material from the bushing 422 at the location of the groove 423, the material that might define the lip is no longer present, eliminating this issue if bushing wear does occur. In some examples, the groove 423 can have a height of between about 0.01 mm to about 0.1 mm, for example, about 0.05 mm.

Any number or variety of components in any of the configurations described herein can be included in an electronic device as described herein. The components can include any combination of the features described herein and can be arranged in any of the various configurations described herein. The structure and arrangement of components of a device, as well as the concepts regarding can apply not only to the specific examples discussed herein, but to any number of embodiments in any combination. Various examples of electronic devices and electronic device components including having various features in various arrangements are described below, with reference to FIGS. 5A-5C.

Figure 5A:
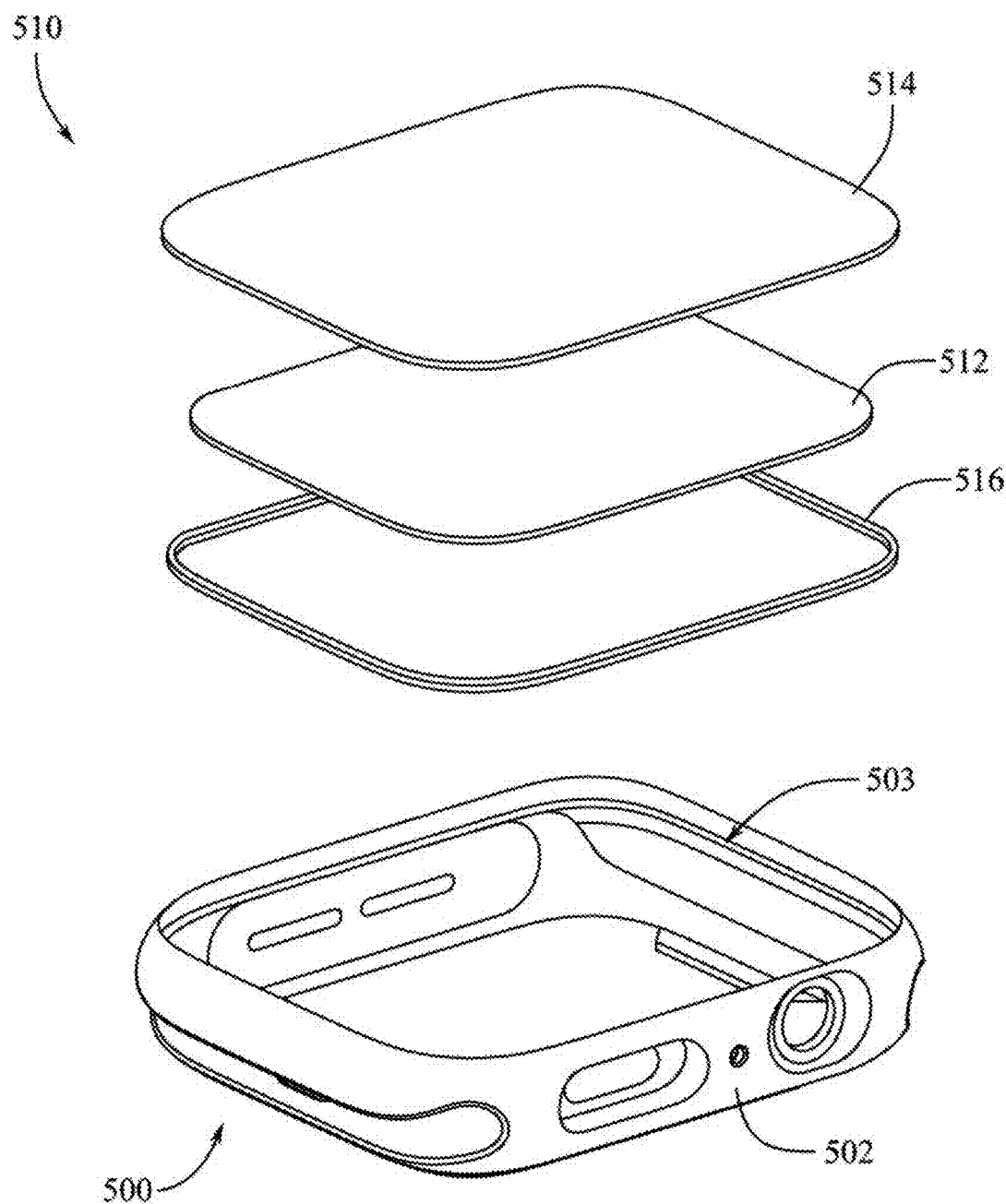
FIG. 5A shows an exploded view of a portion of an electronic device.

FIG. 5A shows an exploded view of several components of an electronic device 500 that can be substantially similar to and can include some or all of the features of the electronic devices described herein. As described with respect to the electronic device 200 of FIG. 2, an electronic device can include a housing 502 that can at least partially define an internal volume and a display assembly 510 that can be retained by the housing. The display assembly 510 can be received by and can be attached to the housing 502, for example, at a feature defined by the housing 502, such as a ledge, lip, or flange 503. The display assembly can include a cover 514 including a transparent material, such as plastic, glass, and/or ceramic. The display assembly 510 can include a display stack 512 that can include multiple layers and components, each of which can perform one or more desired functions. In some examples, a gasket or a seal 516 can be disposed between the display assembly 510 and the housing 502, for example, at the ledge 503, to substantially define a barrier to the ingress of liquids or moisture into the internal volume from the external environment at the location of the seal 516.

Figure 5B:
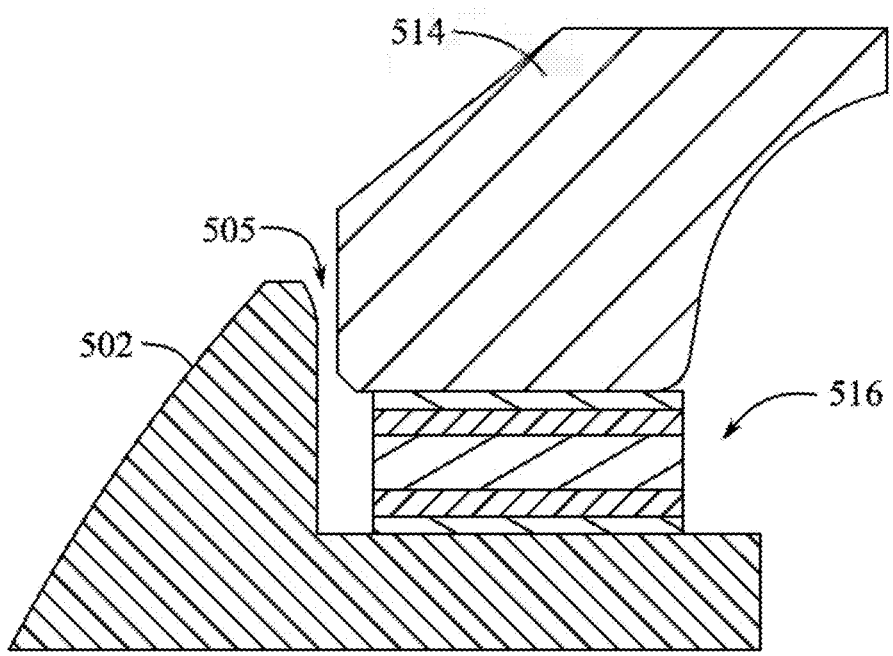
FIG. 5B shows a cross-sectional view of the electronic device of FIG. 15A.

FIG. 5B shows a cross-sectional view of the housing 502, with the transparent cover 514 and seal 516 attached to the housing in an assembled configuration. As can be seen, the seal 516 can be in contact with the transparent cover 514, and the housing 502 and can fix or secure these two components together. In some examples, the seal 516 can include multiple layers of material. As described herein, the seal 516 can include polymer, metal, and/or ceramic materials. In some examples, the seal 516 can substantially surround a periphery of an aperture defined by the housing 502, and can have a shape corresponding to a peripheral shape of one or more portions of the display assembly 510.

Figure 5E:
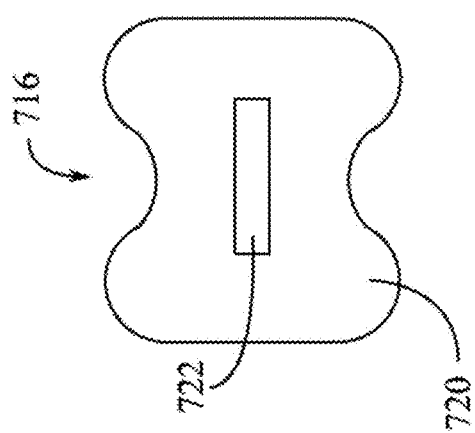
FIG. 5E shows a cross-sectional view of a component of an electronic device.
Figure 5D:
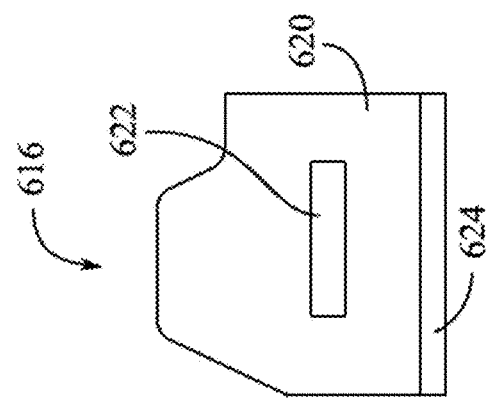
FIG. 5D shows a cross-sectional view of a component of an electronic device.
Figure 5C:
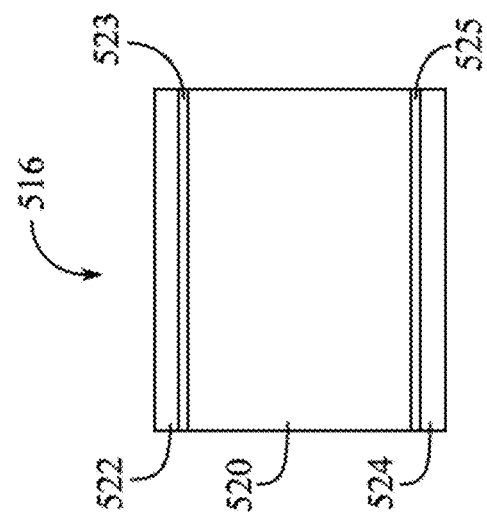
FIG. 5C shows a cross-sectional view of a component of an electronic device.

FIG. 5C shows a cross-sectional view of the seal 516, for example, as shown in FIGS. 5A and 5B. In some examples, the seal 516 can include multiple layers of material bonded or joined together in a stacked configuration. In some examples, the seal 516 can include a silicone layer 520, such as a silicone rubber layer. The silicone layer 520 can be the middle layer or core of the seal 516, and can have a thickness of between about 50 microns and about 300 microns, or between about 100 microns and about 200 microns, for example, about 150 microns. In some examples, the silicone layer 520 can be substantially transparent. The silicone layer 520 can have a hardness of greater than about 5, greater than about 10, or greater than about 15 or more on the Shore A hardness scale.

In some examples, polymer layers 523 and 525 can be disposed on the top and bottom surfaces of the silicone layer 520. These polymer layers 523, 525 can be the same or different materials, and in some examples, can include polyimide. In some examples, the polymer layers 523, 525 can be transparent or translucent. In some examples, the polymer layers 523, 525 can be a colored translucent material, such as a translucent amber colored material. In some examples, the polymer layers 523, 525 can be the same or different thicknesses. The polymer layers 523, 525 can have thicknesses between about 25 microns and about 150 microns, or between about 50 microns and about 100 microns, for example, about 75 microns.

In order to secure the cover 514 to the housing 502 as shown in FIG. 5B, in some examples, the top and bottom exterior surfaces of the seal can be defined by adhesive layers 522, 524. These adhesive layers can be the same or different material, and can have the same or different thicknesses. In some examples, the adhesive layers 522, 524 can include a pressure sensitive adhesive material. The adhesive layers 522, 524 can have thicknesses between about 10 microns and about 100 microns, or between about 25 microns and about 75 microns, for example, about 50 microns. The adhesive layers 522, 524 can have a hardness of greater than about 5, greater than about 10, greater than about 12, or greater than about 15 or more on the Shore A hardness scale.

Thus, in some examples, the entire seal 516 can have a thickness of between about 200 microns and about 600 microns, or between about 300 microns and about 600 microns, for example, about 400 microns. Further, the seal can have a width of between about 500 microns and about 1500 microns, or between about 750 microns and about 550 microns, for example, about 900 microns.

Referring again to FIG. 5B, the width of the seal 516 and/or the width of the adhesive bond of the adhesive layers 522, 524 can be important for increasing the chemical resistance of the seal 516 and preventing corrosion of the seal 516 and/or ingress of liquid or contaminants into the internal volume therethrough. As shown, the housing 502 and the cover 514 can define a gap 505 therebetween. In some examples, this gap can provide for a certain amount of sway or movement of the cover 514 relative to the housing 502, such as during high force events or drop events. This sway and/or compression of the seal 516 can reduce the risk of forces being transmitted through the housing 502 to the cover 514, thereby reducing the risk of damage to the cover 514.

In some examples, however, liquids, particles, contaminants, and/or corrosive materials can inadvertently enter the gap 505, and can come in contact with the seal 516. Thus, it can be desirable for the seal 516 to be corrosion resistant and for the bond length between the seal 516 and the housing 502 and cover 514 to be relatively large.

FIGS. 5D and 5E illustrate cross-sectional views of alternative seal designs 616 and 716. In some examples, a seal 616 can include a relatively stiff core material 622 surrounded by a relatively soft or compliant material 620. In some examples, the core 622 can include one or more metals and/or polymers, such as stainless steel. The core 622 can then be overmolded with a polymer material 620, such as a silicone material in any desired shape. In some examples, one or more layers of adhesive 625 can be disposed on one or more surfaces of the silicone layer 620 to adhere the seal 616 to components, such as a housing or cover.

The seal 616 can also include a core 622 that can include one or more metals and/or polymers, such as stainless steel, and that can be overmolded with a polymer material 620, such as silicone. As shown, the seal 616 can have a substantially X-shaped cross-section, for example, defining one or more indentations or divots that can extend partially or entirely along one or more surfaces of the seal 616. In some examples, the shape of the seal 616 can allow for desired levels of compression or deformation of the seal 616 to effectively dissipate energy and to provide a desired level of sealing between components.

Any number or variety of components in any of the configurations described herein can be included in an electronic device, as described herein. The components can include any combination of the features described herein and can be arranged in any of the various configurations described herein. The structure and arrangement of components of a device, as well as the concepts regarding the function and use thereof can apply not only to the specific examples discussed herein, but to any number of embodiments in any combination. Various examples of electronic devices and electronic device sensor components including having various features in various arrangements are described below, with reference to FIGS. 6A-7B.

Figure 6A:
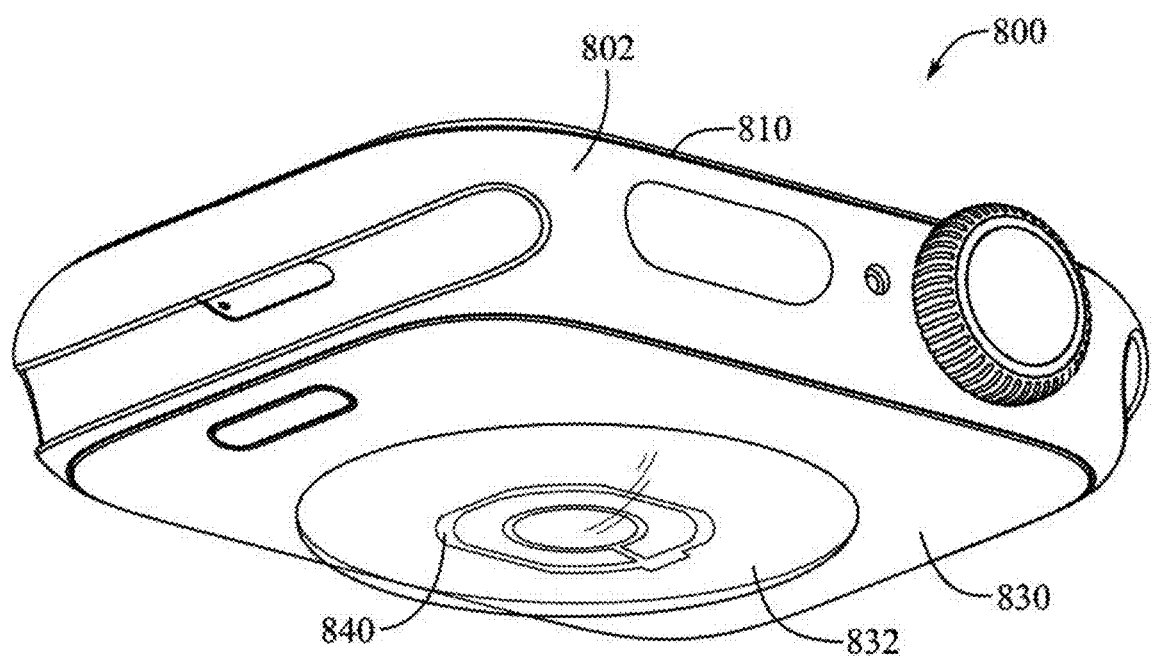
FIG. 6A shows a bottom perspective view of an electronic device.

FIG. 6A shows a bottom perspective view of an electronic device 800 that can be substantially similar to, and can include some or all of the features of the electronic devices described herein. The device 800 can include a back cover 830 that can be attached to the housing 802, for example, opposite the display assembly 810. The back cover 830 can include ceramic, plastic, metal, or combinations thereof. In some examples, the back cover 830 can include an at least partially electromagnetically transparent component 832. The electromagnetically transparent component 832 can be transparent to any desired wavelengths of electromagnetic radiation, such as visible light, infrared light, radio waves, or combinations thereof. In some examples, the electromagnetically transparent component 832 can allow sensors and/or emitters disposed in the housing 802 to communicate with the external environment. In some examples, the electromagnetically transparent component 832 and/or back cover 830 can allow one or more antennas disposed in the internal volume, such as antenna 840, to emit and/or receive electromagnetic radiation, as described further herein. Together, the housing 802, display assembly 810, and back cover 830 can substantially define an internal volume and an external surface of the device 800.

Figure 6B:
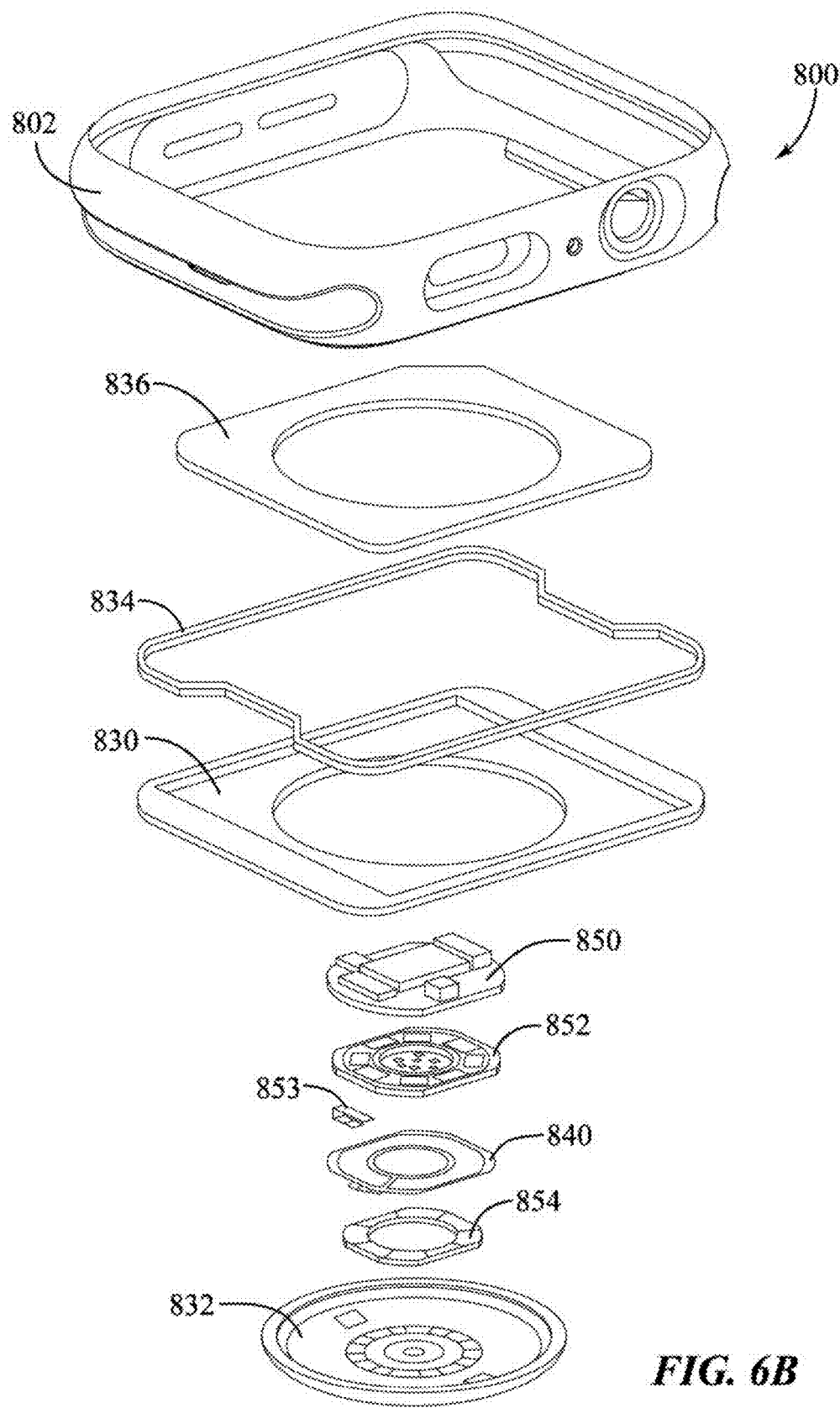
FIG. 6B shows an exploded view of a portion of an electronic device.

FIG. 6B shows an exploded view of components of the electronic device 800. The electronic device 800 can include additional components as described herein, which have been omitted from FIG. 6B for simplicity. In some examples, the back cover 830 can carry a number of components thereon, such as a first antenna element 836, a logic board 850, a sensing package and/or sensor module 852 and a light directing component 854, a second antenna element 840, and a connection component 853 to electrically connect the second antenna element 840 to one or more components of the device 800, such as the logic board 850. In some examples, one or more of these components, such as the sensor module 852 and the second antenna 840, can be disposed over the electromagnetically transparent portion 832 of the back cover 830. In some examples, a seal 834 can be disposed between the back cover 830 and the housing 802 to provide or define a barrier between the internal volume and the ambient environment, as described herein. Further details of the second antenna 840, also referred to as a sensing antenna 840, are described with respect to FIG. 6C.

Figure 6C:
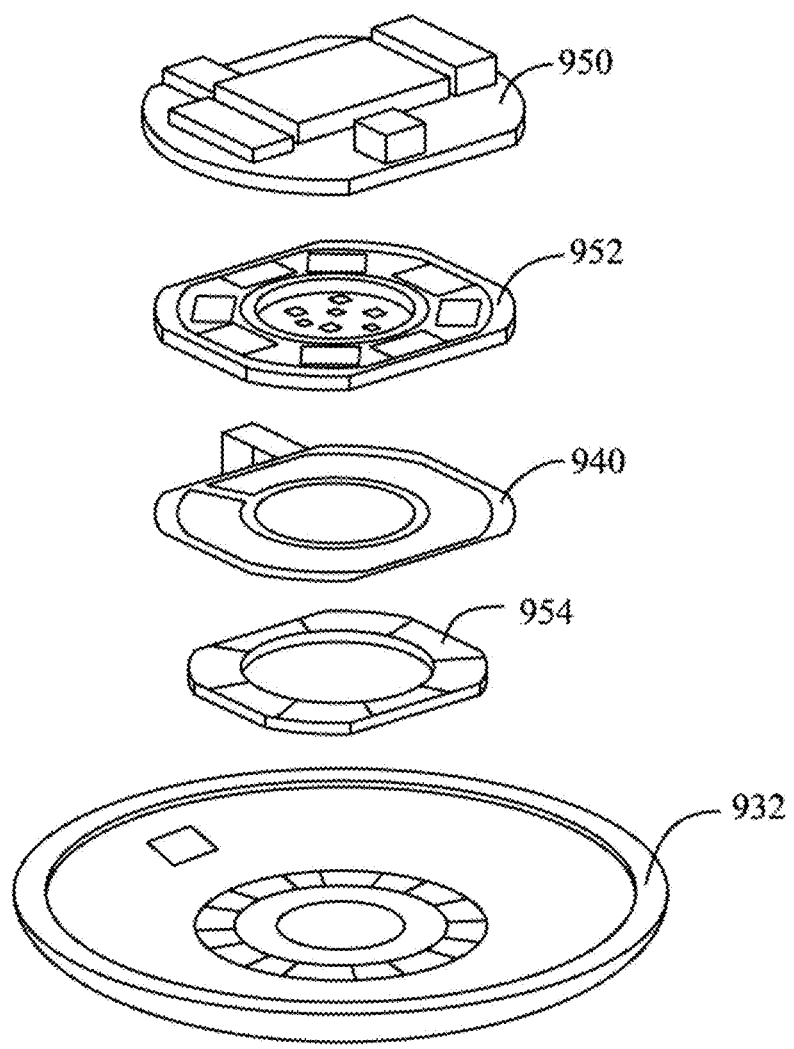
FIG. 6C shows an exploded view of a component of an electronic device.

FIG. 6C shows an exploded view of several components of an electronic device, such as the electronic device 800 described with respect to FIGS. 6A and 6B. In some examples, a device can include a back cover (omitted for simplicity) including an electromagnetically transparent portion 932, as described herein. The device can also include a logic board 950 that can include a substrate, such as a printed circuit board substrate, and can have one or more electronic and/or operational components thereon, such as one or more processors, memory, sensors, and/or integrated circuits. As described with respect to device 800, an electronic device can also include a sensor module 952, a sensing antenna 940, and a light directing component 954 disposed in the internal volume, for example, overlying the electromagnetically transparent portion 932. In some examples, the sensor module 952 can include one or more light emitting and/or sensing components, as described further herein. The light directing component 954 can direct light that is emitted and/or that will be received by the sensor module 952.

In some examples, the sensing antenna 940 can be used to determine a presence of a material at or near the exterior surface of an electronic device including the sensing antenna, for example, at or near an exterior surface at least partially defined by the electromagnetically transparent portion 932. In use, the sensing antenna 940 can be in electrical communication with one or more other components of the device and can be driven to emit and/or reflect electromagnetic radiation at one or more desired frequencies. In some examples, the sensing antenna 940 can radiate energy at about 2.4 GHz, although substantially any frequency can be used. The device can also include an integrated circuit, for example, disposed on the logic board 950, another logic board of the device, such as a main logic board, or at any desired location.

In use, the sensing antenna 940 is driven at a desired frequency, and an associated sensing integrated circuit in the device can measure the performance, efficiency, and/or resonance of the sensing antenna 940. In some examples, a sensing integrated circuit can measure a difference between a power used to drive the antenna and a transmitted power at the location of the sensing integrated circuit. In some examples, a sensing integrated circuit can measure a level of reflected power from the driven antenna, or a level of reflectance, based on a signal and/or power used to drive the antenna. In some examples, the sensing integrated circuit can be located near the back cover of the device, for example, on the logic board 950. Consequently, the sensing integrated circuit can measure antenna efficiency and/or performance in a direction extending out of the back cover and/or electromagnetically transparent component 932. In some examples, the device can include any number of desired sensing integrated circuits, positioned at any number of locations within the internal volume of the device.

As a material or object is brought near the device, for example, near the electromagnetically transparent component 932, the dielectric properties, or permittivity of the material or object can affect the performance, efficiency, and/or resonance of the sensing antenna 940 because at least some of the material or object can be in the transmission path between the sensing antenna 940 and the sensing integrated circuit and/or because a change in the dielectric properties of the region now including the material or object can shift the resonance or resonant frequency of the antenna. The presence of a material or object having a permittivity different than air in the transmission path can result in a tuning and/or detuning of the sensing antenna 940 performance, which is then measured by the sensing integrated circuit, for example, by measuring a change in the transmitted efficiency and/or level or reflectance from the antenna. The degree to which the performance, efficiency, tuning, and/or resonance of the sensing antenna 940 is changed can be measured and can be used to at least partially determine a presence and/or proximity of an object or material near the device. In some examples, the degree to which the performance, efficiency, tuning, and/or resonance of the sensing antenna 940 is changed can be used to at least partially determine a composition of the material and/or object.

In some examples, this proximity detecting functionality can be used to assist the device in determining whether it is actively being worn by a user or whether the device has been removed from a user's wrist. That is, the sensing antenna 940 and the sensing integrated circuit can detect a presence and/or proximity of a body part at or near the device. In some examples, the sensing antenna 940 and the sensing integrated circuit can distinguish the presence of a body part at or near the device from the presence of a different object or material, such as a table. In this way, a user can initially authenticate themselves when the device, such as a smartwatch, is put on, and the device may not require further authentication until the device determines that it has been removed from the user's wrist.

In some examples, the sensing antenna 940 can include a conductive material that is substantially surrounded and/or encapsulated by an insulating material. In some examples, the conductive material can include a metal or metal alloy, such as copper. In some examples, the insulating material can include a polymer material. In some examples, the insulating material can include an adhesive material, such as a pressure sensitive adhesive material. The pressure sensitive adhesive material can aid in fixing the sensing antenna 940 in a desired location, and can further assist in securing other components in the device. In some examples, the sensing antenna 940 can have a substantially annular or ring shape, as shown. In some examples, the sensing antenna 940 can be a monopole antenna, a dipole antenna, or any desired antenna topology. Further, in some examples, a spring finger or connection component can be in electrical communication with the conductive material of the sensing antenna 940 and one or more other components of the device, such as a component that can provide power to and can drive the sensing antenna 940. In some examples, the sensing antenna 940 can include a first layer of pressure sensitive adhesive, a layer of copper, and a second layer of pressure sensitive adhesive overlying the copper and the first layer of pressure sensitive adhesive.

In some examples, the sensing antenna 940 can include any conductive material in any shape or configuration as desired. In some examples, the sensing antenna 940 can be a pre-formed component including conductive material that is disposed in the internal volume of the electronic device. In some examples, however, the sensing antenna 940 can be deposited, plated, or otherwise formed onto another component of the electronic device. For example, a conductive material can be deposited in a desired shape or configuration onto the electromagnetically transparent portion 932 to form the sensing antenna 940. In some examples, the sensing antenna 940 can be formed by a vapor deposition and/or plating process, such as a physical vapor deposition and/or electroplating process. Further, in some examples, an existing antenna of the electronic device can be used or can function as the sensing antenna 940. That is, an electronic device can include one or more antennas, such as a cellular antenna, NFC antenna, LTE antenna, a Wi-Fi antenna, a Bluetooth antenna, and/or a GPS antenna, and one or more of these antennas can additionally or alternatively be driven or used as the sensing antenna. In some examples, any antenna positioned adjacent to, or near the back cover of the device, and/or the electromagnetically transparent portion 930 can be used as the sensing antenna.

Figure 6E:
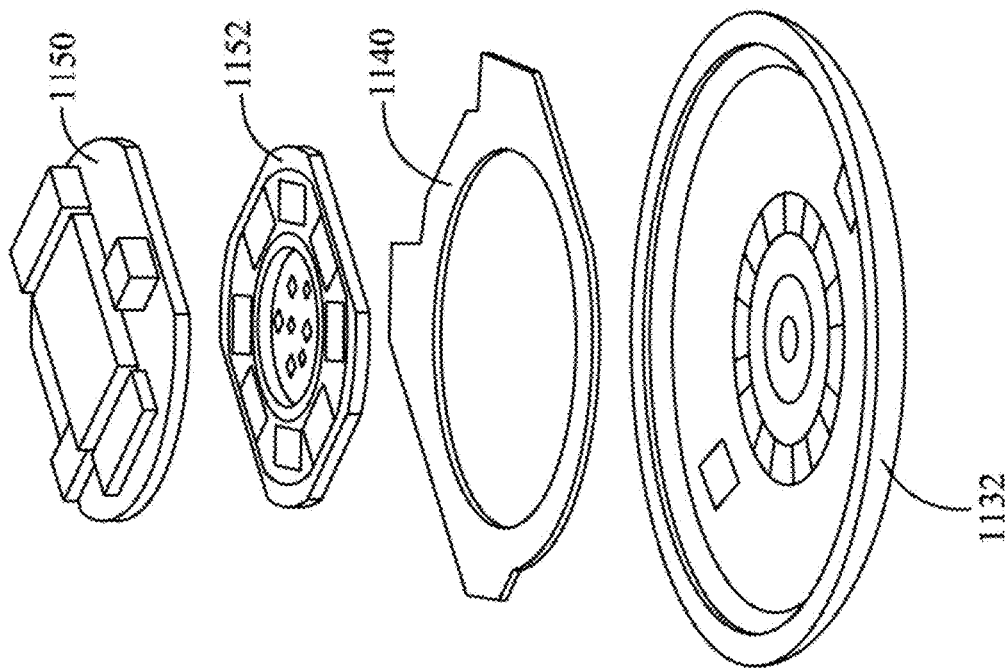
FIG. 6E shows an exploded view of a component of an electronic device.
Figure 6D:
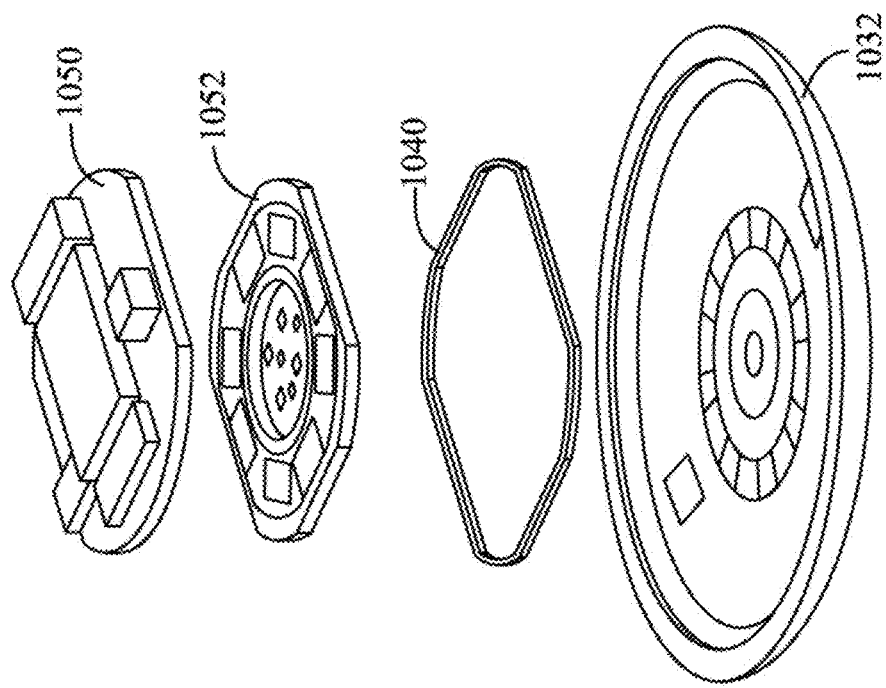
FIG. 6D shows an exploded view of a component of an electronic device.

FIG. 6D shows an exploded view of several components of an electronic device, such as the electronic device 800 described with respect to FIGS. 6A and 6B. As with the example shown in FIG. 6C, an electronic device can include a logic board 1050, a sensor module 1052, and a sensing antenna 1040, for example, overlying the electromagnetically transparent portion 1032. The sensing antenna 1040 can be substantially similar to, can include some or all of the features of, and can function similarly to the sensing antennas described herein. In some examples, the sensing antenna 1040 can include a polymer or plastic material, such as a thermoplastic material. In some examples, the sensing antenna 1040 can also include a conductive material, for example, in a desired design or configuration, integrated into the polymer material. In some examples, the sensing antenna 1040 can be formed by a laser direct structuring (LDS) process. That is, a polymer material including a non-conductive metallic inorganic compound can be exposed to a laser in a desired pattern to write the antenna trace onto or into the polymer material which had previously be molded into a desired shape. Thus, in some examples, the sensing antenna 1040 can be shaped to fit next to and/or around one or more other components of the device, such as the sensor module 1052, and/or the logic board 1050. The entire package, including the logic board 1050, sensor module 1052, and sensing antenna 1040 can then be adhered in place, for example, to the electromagnetically transparent portion 1032.

FIG. 6E shows an exploded view of several components of an electronic device, such as the electronic device 800 described with respect to FIGS. 6A and 6B. As with the examples shown in FIGS. 6C and 6D, an electronic device can include a logic board 1150, a sensor module 1152, and a sensing antenna 1140, for example, overlying the electromagnetically transparent portion 1132. In the present example, the sensing antenna 1140 has been integrated into an existing component of the electronic device that can serve one or more additional functions. For example, the sensing antenna 1140 can include a flexible electrical connector that can be in electrical communication with one or more components of the device. In some examples, the sensing antenna 1140 can include an electromagnetic shielding component, or e-shield. In some examples, an additional trace can be added to the component to form the antenna. For example, an additional trace can be added at or near the portion of the component that defines the central orifice or aperture. Additional details regarding processes for detecting a presence and/or type of material at or near an electronic device are described with respect to FIGS. 7A and 7B.

Figure 7A:
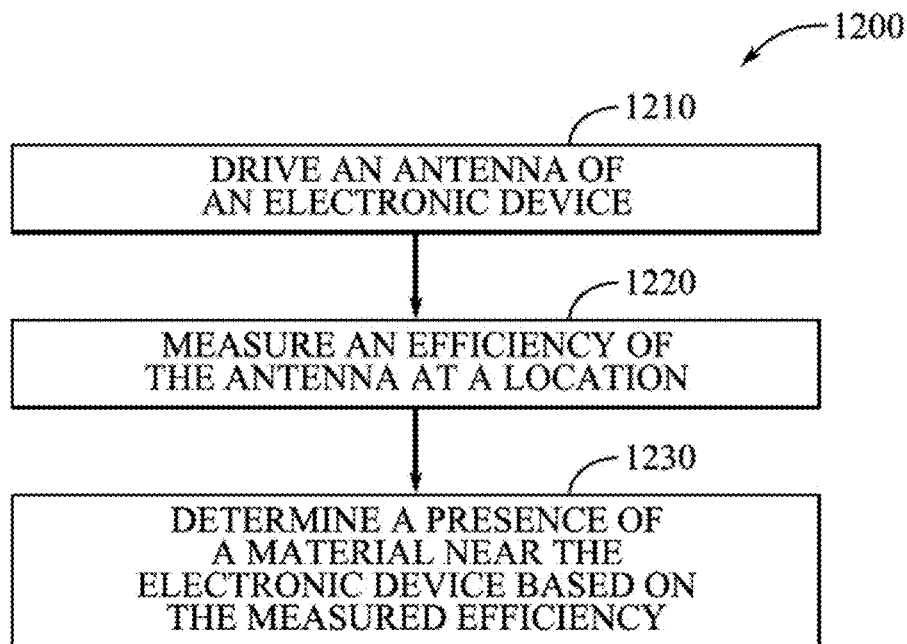
FIG. 7A shows a process flow diagram for a method of detecting a presence of a material near an electronic device.

FIG. 7A shows a process flow diagram for a method 1200 of detecting a presence of a material near an electronic device. In some examples, the method 1200 can be carried out by an electronic device including a sensing antenna and one or more sensing integrated circuits, as described with respect to FIGS. 6A-6D.

At block 1210, an antenna of an electronic device, such as the sensing antennas 940, 1040, 1140 can be driven at one or more desired frequencies and using a desired power. The antenna can be driven by one or more operational components of the device that are in communication with the antenna component.

At block 1220, an efficiency, a level of performance, a level of tuning or detuning of the antenna, and/or a resonance or resonant frequency of the antenna can be measured at one or more locations on or in the electronic device, as described with respect to FIGS. 6A-6D. In some examples, the efficiency of the antenna can be measured at a location such that the transmission path of a signal emitted by the antenna can pass through or near a desired portion of the exterior surface of the electronic device. In some examples, the portion of the exterior surface can be defined by a portion of the back cover and/or transparent cover of the device. In some examples, the efficiency of the antenna can be measured by detecting a transmitted power from the antenna and comparing the transmitted power to the power used to drive the antenna. In some examples, the resonance or resonant frequency of the antenna can be measured by detecting a reflected power from the antenna and comparing the reflected power to the power used to drive the antenna. As used herein, the term transmitted power can be broadly applied to refer to both the power of a signal transmitted or radiated from the antenna, as well as to the reflected power or signal.

At block 1230, a presence of a material at or near an exterior surface of the electronic device can be determined, at least partially, based on the measured efficiency and/or resonance. As described with respect to FIGS. 6A-6D, the presence of a material having a permittivity other than air can affect the transmitted power, efficiency and/or resonance of the antenna. Accordingly, the measured efficiency or resonance can be used to determine a permittivity of the space adjacent to or near an exterior surface of the device, and thus, the presence of a material or object. In some examples, block 1230 can further include determining a type of the material or object that is present at or near the electronic device. For example, block 1230 can further include determining whether an object is conductive or insulating, as well as a level of conductivity. In some examples, block 1230 can include determining whether an object is a user, a metal, a ceramic, a plastic material, organic matter, a liquid, or other types of material.

Figure 7B:
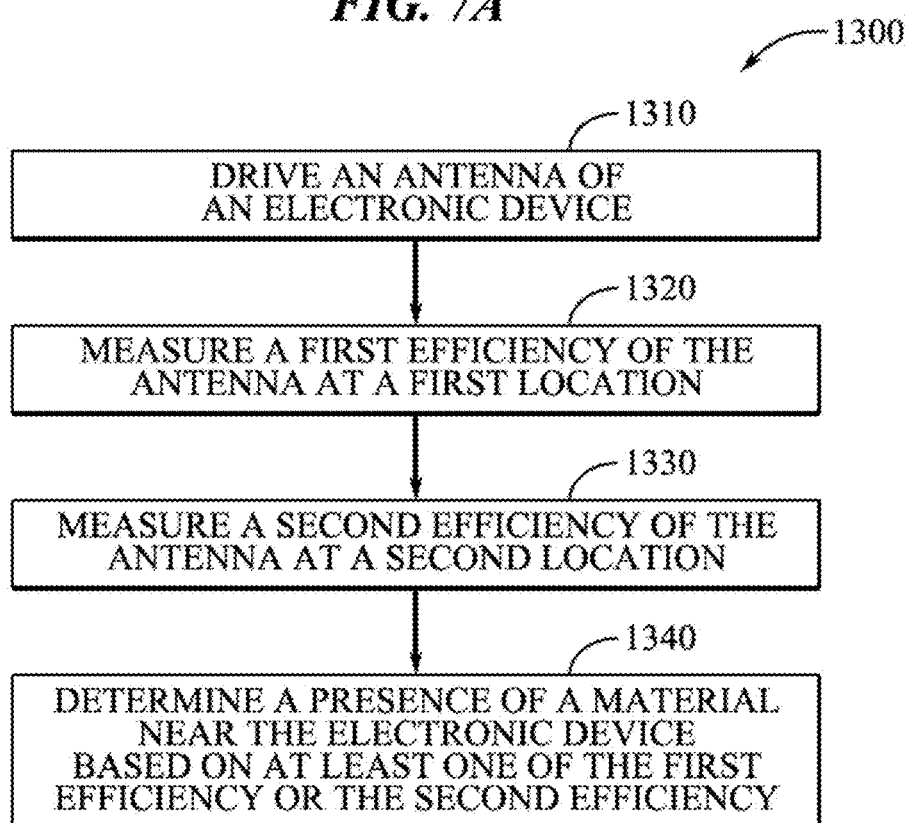
FIG. 7B shows a process flow diagram for a method of detecting a presence of a material near an electronic device.

FIG. 7B shows a process flow diagram for a method 1300 of detecting a presence of a material near an electronic device. In some examples, the method 1300 can be carried out by an electronic device including a sensing antenna and two or more sensing integrated circuits, as described with respect to FIGS. 6A-6D.

At block 1310, an antenna of an electronic device, such as the sensing antennas 940, 1040, 1140 can be driven at one or more desired frequencies and using a desired power. The antenna can be driven by one or more operational components of the device that are in communication with the antenna component.

At block 1320, an efficiency, level of performance, level of tuning or detuning of the antenna, and/or a resonance or resonant frequency of the antenna can be measured at a first location on or in the electronic device, as described with respect to FIGS. 6A-6D. In some examples, the efficiency of the antenna can be measured at a location such that the transmission path of a signal emitted by the antenna can pass through or near a desired portion of the exterior surface of the electronic device. In some examples, the portion of the exterior surface can be defined by a portion of the back cover and/or transparent cover of the device. In some examples, the efficiency of the antenna can be measured by detecting a transmitted power from the antenna and comparing the transmitted power to the power used to drive the antenna. In some examples, the resonance or resonant frequency of the antenna can be measured by detecting a reflected power from the antenna and comparing the reflected power to the power used to drive the antenna. As used herein, the term transmitted power can be broadly applied to refer to both the power of a signal transmitted or radiated from the antenna, as well as to the reflected power or signal.

At block 1330, an efficiency, level of performance, level of tuning or detuning of the antenna, and/or a resonance or resonant frequency of the antenna can be measured at a second, different location on or in the electronic device, as described with respect to FIGS. 6A-6D. In some examples, the efficiency of the antenna can be measured at a location such that the transmission path of a signal emitted by the antenna can pass through or near a desired portion of the exterior surface of the electronic device. In some examples, the portion of the exterior surface can be defined by the other of a portion of the back cover and/or transparent cover of the device as compared to the first location. In some examples, the efficiency of the antenna can be measured by detecting a transmitted power from the antenna and comparing the transmitted power to the power used to drive the antenna. In some examples, the first location can require a transmission path from the antenna to pass through the back cover, while the second location can require a transmission path to pass through the front cover.

At block 1340, a presence of a material at or near an exterior surface of the electronic device can be determined at least partially based on the measured efficiency at the first location and/or the measure efficiency at the second location. As described with respect to FIGS. 6A-6D, the presence of a material having a permittivity other than air can affect the transmitted power and/or efficiency of the antenna. Accordingly, the measured efficiency at one or both of the first and second locations can be used to determine a permittivity of the space adjacent to or near an exterior surface of the device, and thus, the presence of a material or object. In some examples, block 1340 can further include determining a type of the material or object that is present at or near the electronic device. For example, block 1340 can further include determining whether an object is conductive or insulating, as well as a level of conductivity. In some examples, block 1340 can include determining whether an object is a user, a metal, a ceramic, a plastic material, organic matter, a liquid, or other types of material.

In some examples, one or more algorithms stored in the memory of the device can determine whether to determine the presence of the object based on the measured efficiency at the first location, at the second location, and/or by using a weighted combination of the first location and the second location. In some examples where a weight combination of the measured efficiency at the first and second locations is used, an algorithm can determine weights to assign to the efficiencies measured at the first and/or second location. In some examples, the weights can be between 0% and 100%. In some examples, a determination of whether to use the efficiency measured at the first location, at the second location, or a combination of efficiencies measured at the first and second locations, can be based on factors other than the measured efficiencies. These factors are not limited and can include the date or time, a geographical location, input or signals from one or more other sensors, a user input, and others. Additional sensing components and processes can similarly be included.

Figure 8A:
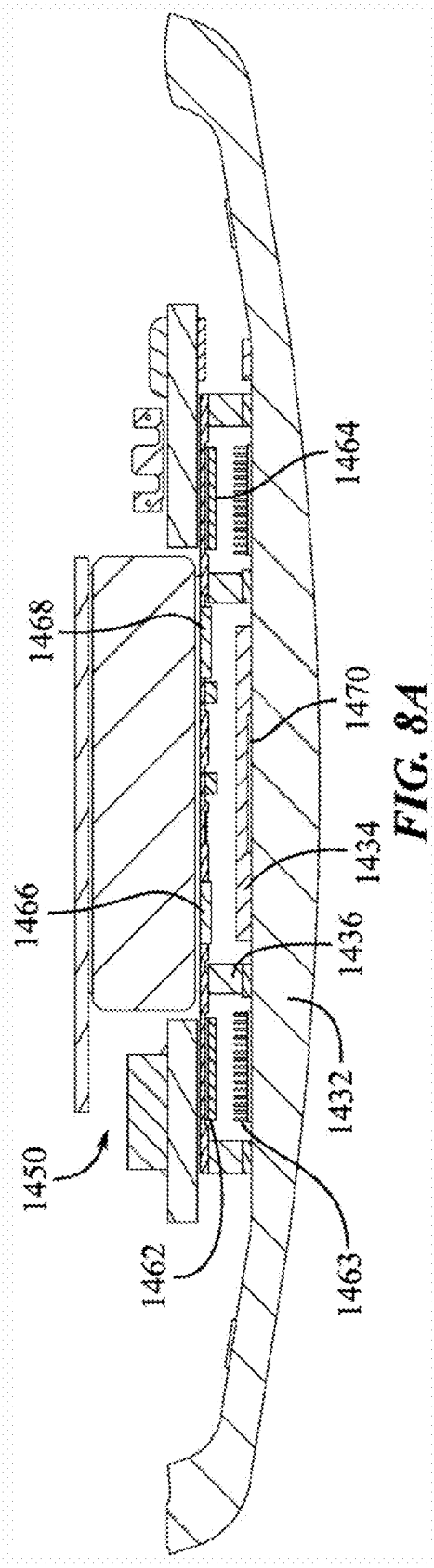
FIG. 8A shows a cross-sectional view of a component of an electronic device.

FIG. 8A shows a cross-sectional view of a portion of an electronic device as described herein. The portion includes an electromagnetically transparent component 1432 that can be part of a back cover (omitted for simplicity) of a device as described herein. The device can also include a logic board 1450 mounted on the electromagnetically transparent component 1432. The device can include one or more sensors and/or emitters, either as part of a sensor module as described herein, as part of the logic board 1450, and/or as standalone components. In some examples, the device can include a lens or light directing component 1434 that can be mounted adjacent to the electromagnetically transparent component 1432. In some examples, the lens 1434 can be a Fresnel lens 1434. In some examples, a light blocking component 1470 can be positioned between the lens 1434 and the component 1432 as described further herein.

The device can include light emitting components 1466, 1468. In some examples, the light emitting components 1466, 1468 can include light emitting diodes (LEDs) that can emit light at one or more desired wavelengths. The device can also include light detecting components 1462, 1464 that can be designed and arranged to receive light that has been emitted by LEDs 1466, 1468, that has passed out of the device through the lens 1434 and electromagnetically transparent component 1432, and back into the device through the lens 1434 and electromagnetically transparent component 1432. In some examples, light blocking components, such as component 1436 can substantially optically isolate the LEDs 1466, 1468 from the detectors 1462, 1464 except along desired light paths. In some examples, the device can include a light directing component, or light control component 1463 disposed opposite one or both light detectors 1462, 1464. In some examples, the light control component 1463 can serve to allow only light incident on the light control component 1463 at a certain angle or range of angles to pass through, thereby serving as a filter.

Figure 8B:
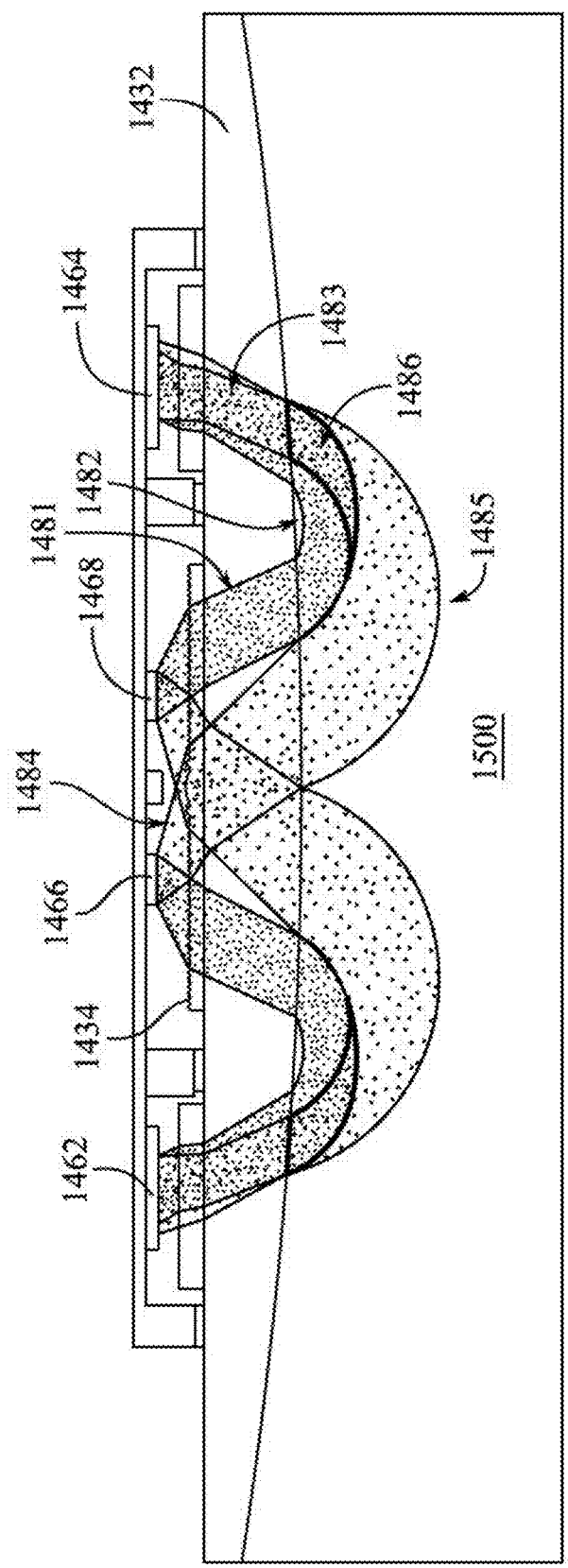
FIG. 8B shows a cross-sectional view of a component of an electronic device adjacent to a user.

FIG. 8B shows the device including the components described with respect to FIG. 8A positioned adjacent to a medium 1500, such as the extremity of a user. As used herein, the term medium can refer to any material, substance, and/or object in any state or combinations of states of matter. For example, air, water, and/or a human body can all be considered mediums as used herein.

The light paths from the LEDs 1466, 1468 to the detectors 1462, 1464 are shown. In some examples, light that is emitted from the LEDs 1466, 1468 and that passed into a user's body, and is then reflected back to the detectors 1462, 1464 can be used to determine one or more physiological and/or biological properties of the user. In some examples, however, the determination of the physiological and/or biological property can be based receiving light that has passed through desired depths of tissue. For example, light emitted from LED 1468 and received by detector 1464 can penetrate a certain depth, while light emitted from LED 1466 and received by detector 1464 can reach a different depth. Difficulties can arise, however, when these two light paths overlap within the user's tissue, potentially introducing noise and making it more difficult to distinguish whether light as been emitted from detector 1466 or 1468. Accordingly, it can be desirable to reduce an amount of overlap of light paths within the user's tissue.

In the example shown in FIG. 8B, the electromagnetically transparent component 1432 can include a ceramic material, such as sapphire, that has a relatively high index of refraction. As shown, light emitted by the LED 1468 can travel along light path 1481, into the user's body along path 1482, and back to the detector 1464 along light path 1483. As seen, light emitted from the LED 1466 can travel along light path 1484, into the user's body along light path 1485, and out to the detector 1464. The relatively high index of refraction of the ceramic or sapphire component 1432 can mean that the overlap region 1486 of the light paths within the user's tissue is relatively small, for example less than about 5%, 4%, 3.5%, or even less than about 3% of the volume of tissue illuminated. This amount of overlap can be accounted for through algorithms or other noise reduction techniques and can produce results having a desirable level of accuracy.

Figure 8C:
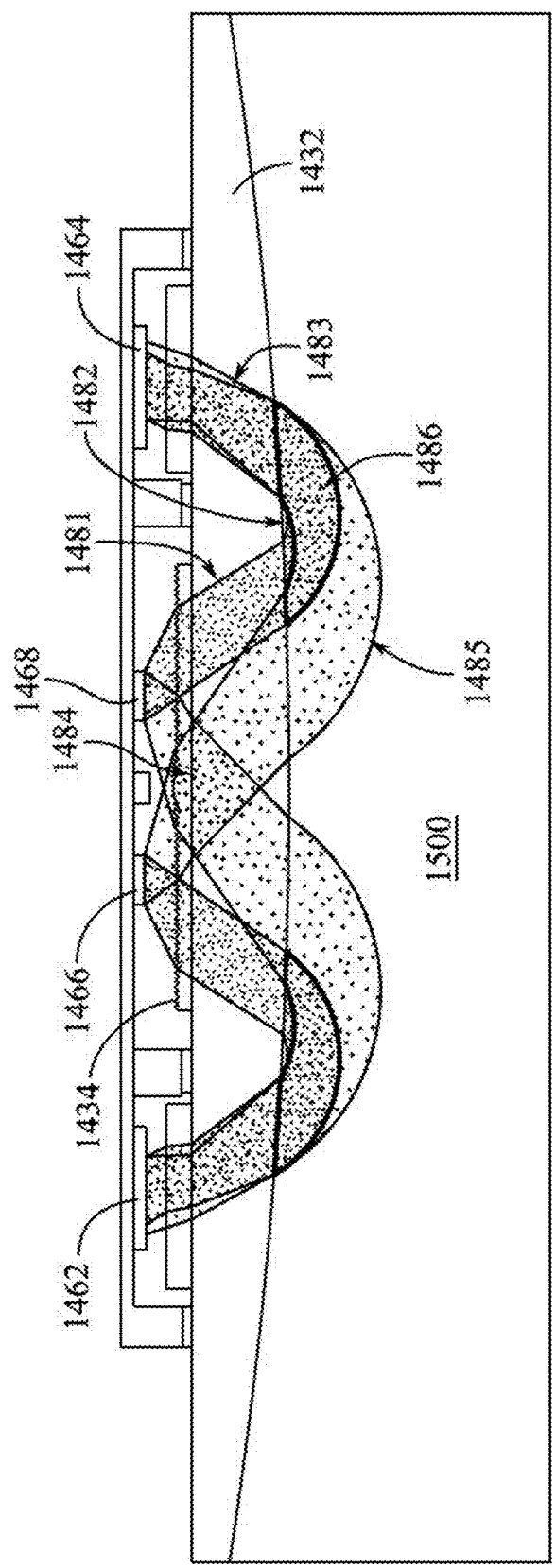
FIG. 8C shows a cross-sectional view of a component of an electronic device adjacent to a user.

FIG. 8C shows a cross-sectional view of the same components as illustrated in FIG. 8C, however the component 1432 now includes a material having a relatively lower refractive index, such as glass. As can be seen, the lower index of refraction can result in a significantly higher area or volume of overlap 1486. For example, the volume of overlap can be greater than 15%, greater than 20%, or even greater than 25% of the volume of tissue illuminated. Thus, while a component 1432 that includes glass can provide benefits to the device, such as reduced material cost, reduced manufacturing cost, increased durability, ease of component replacement, and other benefits, the use of glass can have an undesirable effect on the determination of one or more biological and/or physiological properties of the user.

Figure 8D:
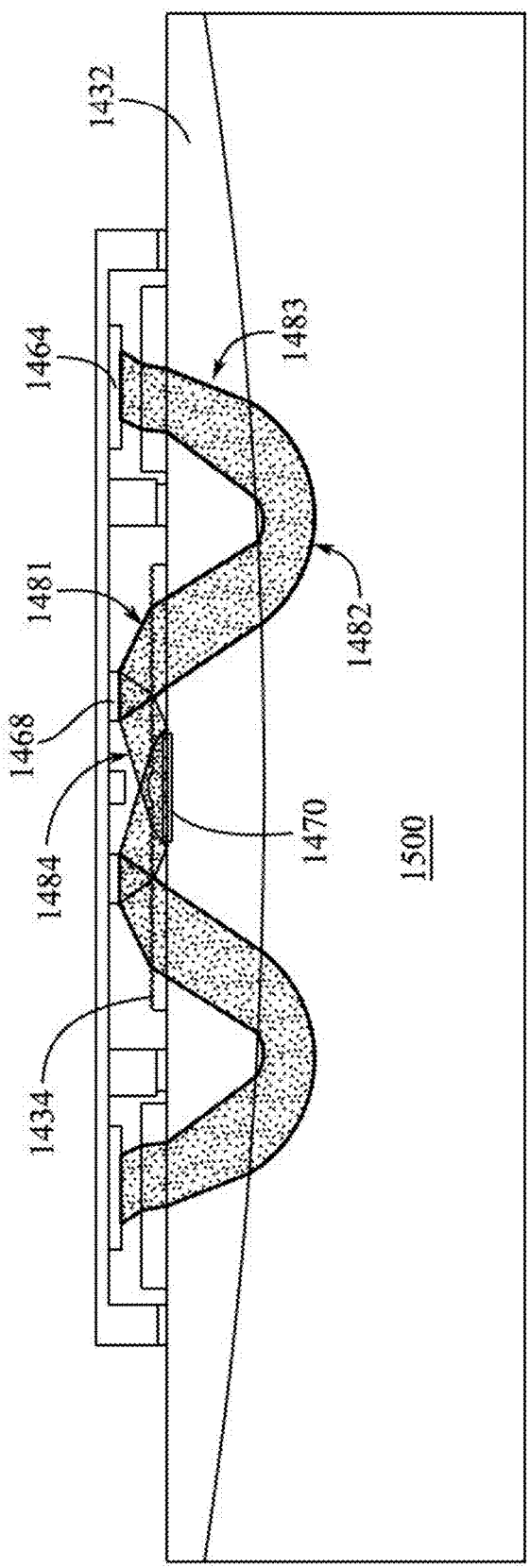
FIG. 8D shows a cross-sectional view of a component of an electronic device adjacent to a user.

Accordingly, as shown in FIG. 8D, a light blocking component 1470 can be positioned on an interior surface of the component 1432 to block some or substantially all of the light emitted from the LED 1466 that would otherwise reach the detector 1464 and/or overlap with light emitted from the LED 1468. In this way, the overlap volume can be less than about 5%, 4%, 3.5%, or even less than about 3% of the volume of tissue illuminated even with a component 1432 that includes glass or some other relatively low refractive index material. In some examples, the light blocking component 1470 can be positioned directly on the component 1432, for example between the component 1432 and the Fresnel lens 1434. In some examples, the light blocking component 1470 can be positioned substantially in the center of the component 1432.

In some examples, the light blocking component 1470 can take the form of a dot or circular portion of ink or other material that can be opaque to one or more desired wavelengths, or ranges of wavelengths of light. In some examples, the light blocking component 1470 can be opaque to visible light, that is light having wavelengths between about 380 nm and about 740 nm. In some examples, the light blocking component 1470 can be opaque to wavelengths of light emitted by the LEDs 1466, 1468. In some examples, the LEDs 1466, 1468 can emit green light and thus the light blocking component 1470 can be opaque to a range of wavelengths of light including green light. That is, in some examples, the light blocking component 1470 can be opaque to light including light having wavelengths between about 520 nm and about 560 nm. In some examples, the light blocking component 1470 can, in some examples, be transparent to one or more other wavelengths of light, so as not to affect the functionality of other sensors, emitters, and/or detectors of the device, such as those which might utilize infrared wavelengths, or light having wavelengths between about 740 nm and about 1 mm. In some examples, the ink or material of the light blocking component 1470 can have a thickness of about 15 microns or less, about 10 microns or less, about 7 microns or less, about 5 microns or less, or even about 2 microns or less. In some examples, the light blocking component 1470 can have a diameter or major dimension of about 10 mm or less, about 5 mm or less, about 4 mm or less, or even about 2 mm or less.

In some examples, the light blocking component 1470 can be deposited on the component 1432 by any combination of printing and/or deposition processes, such as a pad printing and/or one or more physical vapor deposition processes. In some examples, the surface of the component 1432 can be treated prior to forming the light blocking component 1470. For example, a layer of silicon dioxide can be deposited on the surface prior to forming the light blocking component 1470.

Any of the features or aspects of the devices and components discussed herein can be combined or included in any varied combination. For example, the design and shape of the components or devices is not limited in any way and can be formed by any number of processes, including those discussed herein. As used herein, the terms exterior, outer, interior, and inner are used for reference purposes only. An exterior or outer portion of a component can form a portion of an exterior surface of the component, but may not necessarily form the entire exterior of outer surface thereof. Similarly, the interior or inner portion of a component can form or define an interior or inner portion of the component, but can also form or define a portion of an exterior or outer surface of the component.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "including."

To the extent applicable to the present technology, gathering and use of data available from various sources can be used to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, TWITTER® ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

What is claimed is:

1. An electronic device, comprising:
a housing at least partially defining an internal volume, the housing comprising an optically transparent component at least partially defining an exterior surface of the electronic device;
a first light emitter positioned in the internal volume;
a second light emitter positioned in the internal volume;
a light detector positioned in the internal volume, the light detector optically isolated from the first light emitter and the second light emitter within the internal volume; and
an opaque material disposed on the optically transparent component, the opaque material positioned between the first light emitter and the second light emitter, the opaque material being closer to the exterior surface than the first light emitter and the second light emitter, the opaque material positioned to:
inhibit light emitted from the second light emitter from reaching the light detector along a path from the second light emitter, through a medium adjacent to a portion of exterior surface defined by the optically transparent component, and onto the light detector through the optically transparent component; and
allow light emitted from the first light emitter to reach the light detector along a path from the first light emitter, through the medium, and onto the light detector through the optically transparent component.

2. The electronic device of claim 1, wherein the optically transparent component comprises glass.

3. The electronic device of claim 1, wherein the opaque material is opaque to green light.

4. The electronic device of claim 1, wherein the opaque material is transparent to infrared light.

5. The electronic device of claim 1, wherein the opaque material has a major dimension of 10 mm or less.

6. The electronic device of claim 1, wherein the opaque material has a thickness of 10 microns or less.

7. The electronic device of claim 1, further comprising a lens positioned over the opaque material.

8. The electronic device of claim 1, wherein the optically transparent component comprises sapphire.

9. The electronic device of claim 8, wherein:
the optically transparent component comprises a silicon dioxide layer; and
the opaque material is disposed on the silicon dioxide layer.

10. An electronic device, comprising:
a housing defining an internal volume, the housing comprising an optically transparent portion;
a light emitter disposed in the internal volume;
a first light detector disposed in the internal volume;
a second light detector disposed in the internal volume; and
a light blocking component disposed between the first light detector and the second light detector and on an internal surface of the optically transparent portion, the light blocking component sized and positioned to:
prevent light emitted by the light emitter from passing out of the electronic device through the optically transparent component in a direction oriented more towards the second light detector than the first light detector; and
allow light emitted by the light emitter to pass out of the electronic device through the optically transparent component in a direction oriented more towards the first light detector than the second light detector.

11. The electronic device of claim 10, wherein the light blocking component has a substantially circular shape.

12. The electronic device of claim 11, wherein the light blocking component has a diameter of 10 mm or less.

13. The electronic device of claim 10, wherein the light blocking component comprises a layer of ink.

14. The electronic device of claim 13, wherein the layer has a thickness of about 10 microns or less.

15. The electronic device of claim 10, wherein the light emitter comprises an LED.

16. The electronic device of claim 10, wherein:
the light blocking component comprises a first light blocking component; and
the electronic device further comprises a second light blocking component positioned in the internal volume between the light emitter and the first light detector.

17. A housing for an electronic device, comprising:
a cover defining an aperture;
an optically transparent component positioned in the aperture and secured to the cover, the optically transparent component at least partially defining an internal surface of the housing and an external surface of the housing;
a lens overlying a portion of the optically transparent component defining the internal surface; and
an opaque material disposed on the portion of the optically transparent component defining the internal surface, the opaque material positioned between the optically transparent component and the lens.

18. The housing of claim 17, wherein the opaque material is opaque to visible light and at least partially transparent to infrared light.

19. The housing of claim 17, wherein the lens comprises a Fresnel lens.

20. The housing of claim 17, wherein the optically transparent component comprises glass.

\* \* \* \* \*